United States Patent
Cowe et al.

(10) Patent No.: US 11,541,178 B2
(45) Date of Patent: Jan. 3, 2023

(54) MEDICAMENT DELIVERY DEVICE AND SYSTEM

(71) Applicant: Owen Mumford Limited, Woodstock (GB)

(72) Inventors: Toby Cowe, Oxfordshire (GB); Colin Webb, Oxfordshire (GB)

(73) Assignee: Owen Mumford Limited, Oxfordshire (GB)

( * ) Notice: Subject to any disclaimer, the term of this patent is extended or adjusted under 35 U.S.C. 154(b) by 898 days.

(21) Appl. No.: 16/461,728

(22) PCT Filed: Nov. 17, 2017

(86) PCT No.: PCT/GB2017/053469
§ 371 (c)(1),
(2) Date: May 16, 2019

(87) PCT Pub. No.: WO2018/091916
PCT Pub. Date: May 24, 2018

(65) Prior Publication Data
US 2019/0358401 A1 Nov. 28, 2019

(30) Foreign Application Priority Data
Nov. 18, 2016 (GB) .................................. 1619561

(51) Int. Cl.
*A61M 5/20* (2006.01)
*A61M 5/24* (2006.01)
(Continued)

(52) U.S. Cl.
CPC ........ *A61M 5/2066* (2013.01); *A61M 5/2429* (2013.01); *A61M 5/2448* (2013.01);
(Continued)

(58) Field of Classification Search
CPC ............ A61M 5/3294; A61M 5/31596; A61M 5/284; A61M 5/2066; A61M 5/1782;
(Continued)

(56) References Cited

U.S. PATENT DOCUMENTS 3,680,558 A  1/1972 Kapelowitz
6,692,469 B1 *  2/2004 Weekes ................ A61M 5/002
 604/137
(Continued)

FOREIGN PATENT DOCUMENTS

JP  2001511404 A  8/2001
JP  2007014615 A  1/2007
(Continued)

OTHER PUBLICATIONS

First Office Action from corresponding Japanese Patent Application No. 2019-526572 dated Jul. 26, 2021 (12 pages) English translation included.

(Continued)

*Primary Examiner* — Nathan R Price
*Assistant Examiner* — Justin L Zamory
(74) *Attorney, Agent, or Firm* — Quarles & Brady LLP

(57) ABSTRACT

A medicament delivery device system for delivery of a medicament from a cartridge (10). The system comprises a first container (11) for storage of a first substance, a second container (12) received in the first container (11) for storage of a second substance, and valve means (68) for closing a distal end of the second container (12). The system further comprises a disposable cassette (102) and a reusable firing unit (200). The cassette (102) has a body (104) for receiving the cartridge (10), and a mixing element (148) for displacing the second substance into the first chamber (16) in a mixing stroke, to mix with the first substance to form the medicament. The firing unit (200) comprises a drive element (208)

(Continued)

for expelling the medicament from the first chamber (16) in a delivery stroke and a trigger arrangement (240) for initiating the delivery stroke.

38 Claims, 12 Drawing Sheets

(51) Int. Cl.
*A61M 5/315* (2006.01)
*A61M 5/32* (2006.01)
*A61M 5/00* (2006.01)
*A61M 39/24* (2006.01)

(52) U.S. Cl.
CPC ...... *A61M 5/3158* (2013.01); *A61M 5/31501* (2013.01); *A61M 5/31591* (2013.01); *A61M 5/326* (2013.01); *A61M 5/008* (2013.01); *A61M 5/3204* (2013.01); *A61M 2005/3247* (2013.01); *A61M 2005/3267* (2013.01); *A61M 2039/242* (2013.01); *A61M 2039/2426* (2013.01)

(58) Field of Classification Search
CPC ............ A61M 5/16827; A61M 5/2429; A61M 5/2448; A61M 5/31501; A61M 5/3158; A61M 5/31591; A61M 5/326; A61M 5/008; A61M 5/3204; A61M 2005/3247; A61M 2005/3267; A61M 2039/242; A61M 2039/2426
See application file for complete search history.

(56) References Cited

U.S. PATENT DOCUMENTS

2009/0105637 A1    4/2009   Wang et al.
2011/0313364 A1   12/2011   Rolfe et al.
2016/0263320 A1*   9/2016   Constantineau .... A61M 5/3243

FOREIGN PATENT DOCUMENTS

JP        2009518080 A    5/2009
JP        2012513855 A    6/2012
WO     WO 99/06100    11/1999

OTHER PUBLICATIONS

Mar. 1, 2018 Transmittal of ISR and Written Opinion of Int'l Searching Authority for PCT/GB2017/053469.

* cited by examiner

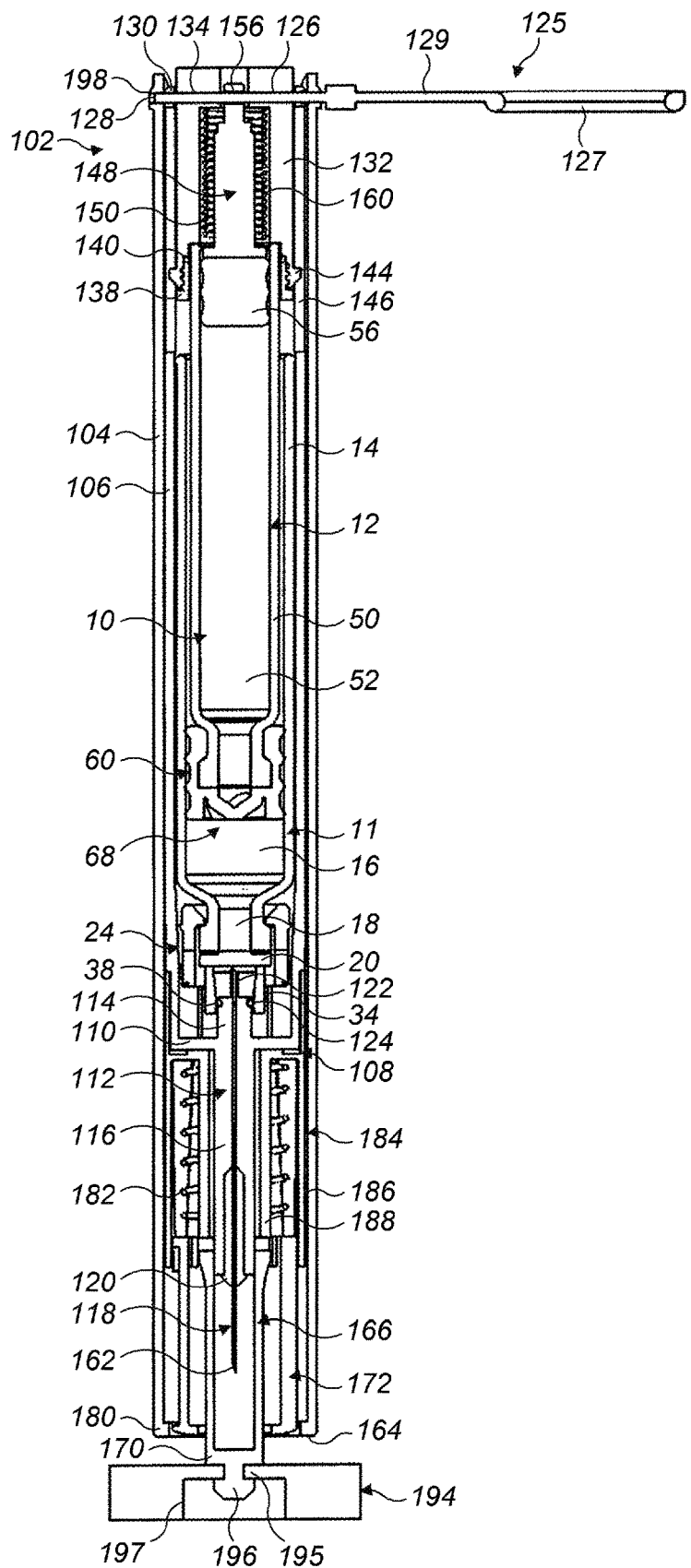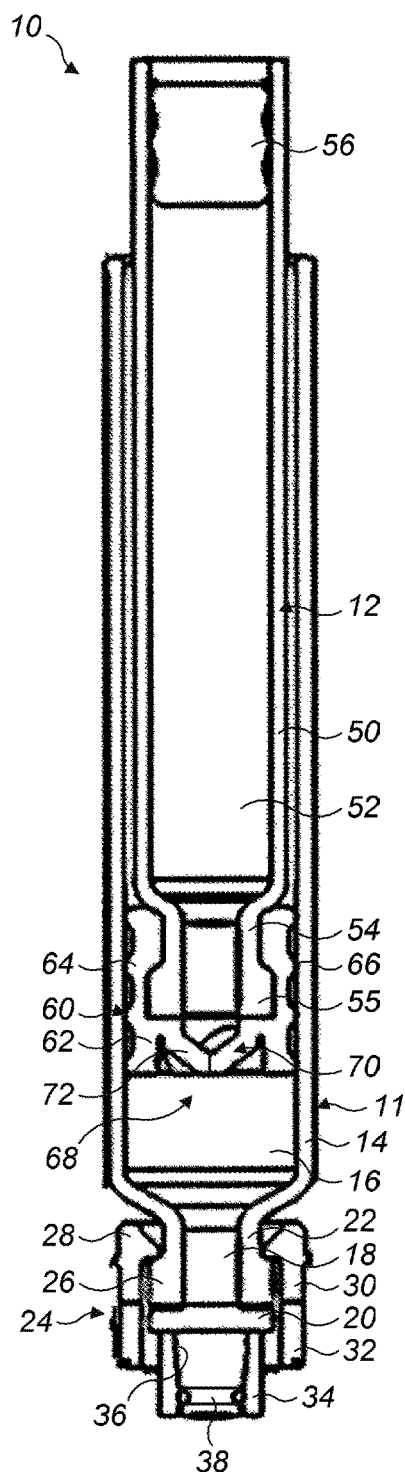
*FIG. 2*  *FIG. 3*

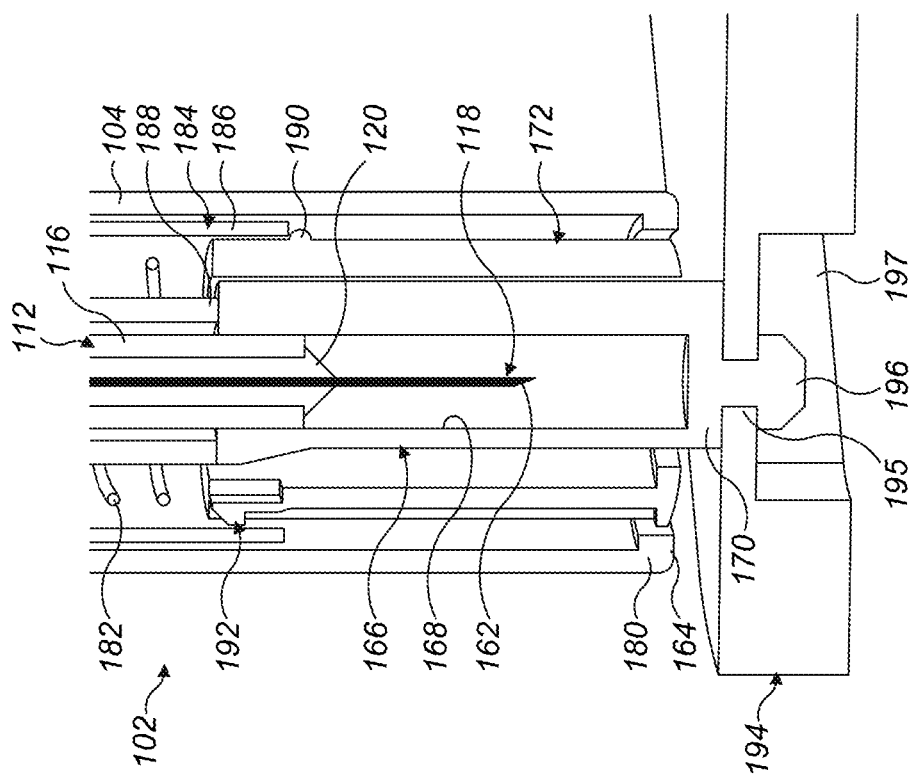
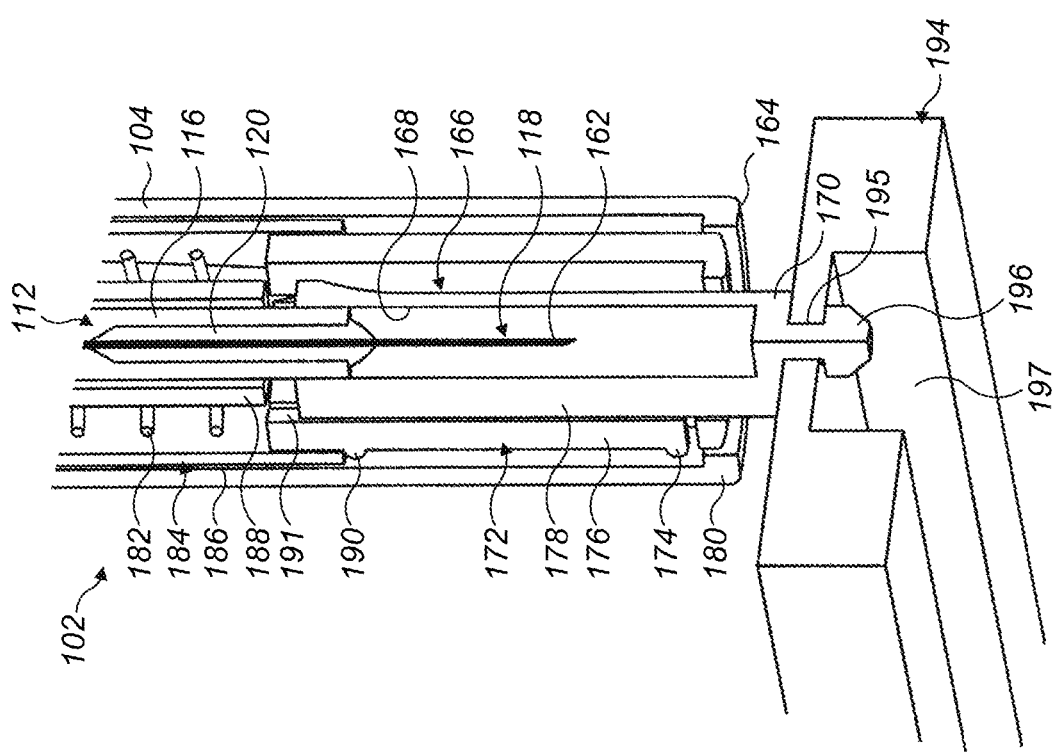
FIG. 5(b)
FIG. 5(a)

MEDICAMENT DELIVERY DEVICE AND SYSTEM

The present application is a § 371 submission of international application no. PCT/GB2017/053469, filed 17 Nov. 2017 and titled Medicament Delivery Device and System, which was published in the English language on 24 May 2018 with publication no. WO 2018/091916 A1, and which claims the benefit of the filing date of GB 16 19561.2 filed 18 Nov. 2016, the contents of which are incorporated herein by reference.

This invention relates to systems and devices suitable for delivery of medicament substances. In particular, but not exclusively, the invention relates to systems and devices for automatic mixing of substances to form a medicament and for automatic delivery of the medicament to a patient. This invention further relates to medicaments, including pharmaceutical compositions, for subcutaneous injection or infusion disposed within the delivery devices and methods of treating patients with conditions susceptible to treatment by delivering the medicament using the delivery devices described herein.

Medicaments for subcutaneous injection or infusion are used in therapy in various different clinical situations. In some cases, it is necessary or advantageous to supply a medicament to a user as two separate components, and to mix the components just prior to use.

For instance, some injectable medicaments, such as blood factors for the treatment of haemophilia and glucagon for the treatment of severe hypoglycaemia, have an unacceptably short shelf-life when in liquid form, and are therefore most commonly supplied in freeze-dried or lyophilised form as a solid powder. In the lyophilised form, the shelf life of the medicament is substantially extended. Prior to use, the medicament must be reconstituted by mixing with a suitable sterile diluent, such as water or saline.

In a conventional arrangement, the solid component of a medicament is supplied in a vial, and the liquid diluent is supplied in a separate syringe. The vial is typically closed with a polymeric membrane or septum that can be pierced by a needle of the syringe. In use, the syringe needle is inserted through the septum, and the diluent is injected into the vial to mix with the solid component. The vial is then shaken to encourage thorough mixing. The syringe may be removed from the vial during shaking, and so the septum is typically self-sealing to prevent leakage of the vial contents once the needle is withdrawn.

After reconstitution of the medicament, the syringe is re-inserted in the vial if necessary and then the mixture is drawn into the syringe. The syringe, now containing the reconstituted medicament, is removed from the vial and can be used to administer the reconstituted medicament to a patient by injection.

This conventional arrangement has several disadvantages. The need to provide a separate vial and syringe, and to keep those components sterile, can be inconvenient. Also, the number of steps involved in and the relatively complex actions required can make the arrangement unattractive in some clinical situations, such as self-administration by a patient at home. Self-administration can be particularly difficult for young patients, or those with reduced manual dexterity.

In the field of single-component, non-reconstitutable liquid medicaments, the problem of providing medicaments in a more convenient form for injection has been addressed by the development of several different types of medicament delivery device.

For example, the need for a separate vial and syringe can be avoided by the use of pre-filled, disposable syringes containing a single dose of the medicament. In one common pre-filled syringe design, sold under the registered trade mark Hypak (Becton Dickinson, N.J., USA), a needle is permanently fixed to the distal end of the syringe body, and the needle is kept sterile by a removable cap.

More sophisticated auto-injector devices designed for self-administration of a single, fixed dose of non-reconstitutable medicament are also known. Typically, in such devices, one or more of needle insertion, medicament delivery, dose indication, needle retraction and deployment of a shroud for shielding the needle after injection are triggered by one or more user operations, such as operating a trigger button or slider. The medicament dose in an auto-injector device may be provided the form of a disposable, pre-filled glass syringe with a fixed needle, such as a Hypak syringe of the type described above, or in a cartridge or other package.

In contrast, relatively few devices suitable for the automatic delivery of reconstitutable medicaments are available. One difficulty in the design of such devices is that multiple different user operations can be required in order to actuate the mixing, insertion and delivery steps. This increases the complexity of operation for users and increases the risk of incorrect operation, for example when the mixing step is not completed correctly before the injection step is performed. It would therefore be desirable to provide a device for the mixing and delivery of reconstitutable medicaments in which the starting substances can be mixed automatically and reliably to reduce the risk of incorrect operation.

Furthermore, whilst auto-injector devices for the delivery of non-reconstitutable medicaments are often relatively simple and low-cost, and are therefore intended for disposal after a single use, the increased complexity of devices for the mixing and delivery of reconstitutable medicaments means that it would be desirable to provide a device for the mixing and delivery of reconstitutable medicaments in which at least a part of the device can be re-used.

Against this background, and from a first aspect, the present invention resides in a medicament delivery device system for delivery of a medicament from a cartridge comprising a first container having a first chamber for storage of a first substance, a second container at least partially received in the first container and having a second chamber for storage of a second substance, and valve means for closing a distal end of the second chamber. The system comprises a disposable cassette and a reusable firing unit that is removably attachable to the cassette. The cassette comprises a body for receiving the cartridge, and a mixing element for displacing the second substance into the first chamber through the valve means in a mixing stroke to mix with the first substance to form the medicament, and the firing unit comprises a drive element for expelling the medicament from the first chamber in a delivery stroke, and a trigger arrangement for initiating the delivery stroke. Medicaments, including pharmaceutical compositions, contemplated for use in the delivery device may comprise small molecules, vaccines, live or attenuated cells, oligonucleotides, DNA, peptides, antibodies, and recombinant or naturally occurring proteins, whether human or animal, useful for prophylactic, therapeutic or diagnostic application. The active ingredient can be natural, synthetic, semi-synthetic or derivatives thereof. A wide range of active ingredients are contemplated. These include, for example,hormones, cytokines, hematopoietic factors, growth factors, antiobesity factors, trophic factors, anti-inflammatory factors, and enzymes. The pharmaceutical compositions also may include, but are not limited to, insulin, gastrin, prolactin, human growth hormone (hGH), adrenocorticotropic hormone (ACTH), thyroid stimulating hormone (TSH), luteinizing hormone (LH), follicle stimulating hormone (FSH), human parathyroid hormone (PTH), glucagon, glucagons-like peptide 1 (GLP-1), glucagons-like peptide 2 (GLP-2), insulin-like growth factors (IGFs) such as insulin growth factor I (IGF I), insulin growth factor II (IGF II), growth hormone-releasing factor (GRF), human chorionic gonadotropin (HCG), gonadotropin-releasing hormone, motilin, interferons (alpha, beta, gamma), interleukins (e.g., IL-1, IL-2, IL-4, IL-5, IL-6, IL-9, IL-11, IL-12, IL-13, IL-15, IL-16, IL-17, IL-18, IL-20 or IL-21), interleukin-1 receptor antagonists (IL-Ira), tumor necrosis factor (TNF), tumor necrosis factor-binding protein (TNF-bp), CD40L, CD30L, erythropoietin (EPO), plasminogen activator inhibitor 1, plasminogen activator inhibitor 2, von Willebrandt factor, thrombopoietin, angiopoietin, granulocyte-colony stimulating factor (G-CSF), stem cell factor (SCF), leptin (OB protein), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), transforming growth factors, epidermal growth factor (EGF), vascular endothelial growth factor (VEGF), macrophage colony stimulating factor (M-CSF), granulocyte macrophage colony stimulating factor (GM-CSF), megakaryocyte derived growth factor (MGDF), keratinocyte growth factor (KGF), platelet-derived growth factor (PGDF), novel erythropoiesis stimulating protein (NESP), bone morphogenetic protein (BMP), superoxide dismutase (SOD), tissue plasminogen activator (TPA), pro-urokinase, urokinase, streptokinase, kallikrein, a protease inhibitor e.g. aprotinin, an enzyme such as asparaginase, arginase, arginine deaminase, adenosine deaminase, ribonuclease, catalase, uricase, bilirubin oxidase, trypsin, papain, alkaline phosphatase, glucoronidase, purine nucleoside phosphorylase or batroxobin, an opioid, e.g. endorphins, enkephalins or non-natural opioids, a neuropeptide, neuropeptide Y, calcitonin, cholecystokinins, corticotrophin-releasing factor, vasopressin, oxytocin, antidiuretic hormones, thyrotropin releasing hormone, relaxin, peptideYY, pancreastic polypeptide, CART (cocaine and amphetamine regulated transcript), a CART related peptide, perilipin, melanocortins (melanocyte-stimulating hormones) such as MSH, melanin-concentrating hormones, natriuretic peptides, adrenomedullin, endothelin, secretin, amylin, vasoactive intestinal peptide (VIP), pituary adenylate cyclase activating polypeptide (PACAP), bombesin, bombesin-like peptides, thymosin, heparin-binding protein, soluble CD4, hypothalmic releasing factor, melanotonins, and human antibodies and humanized antibodies, and other pharmaceutical compositions suitable for administration with the delivery devices. The term proteins, as used herein, includes peptides, polypeptides, consensus molecules, analogs, derivatives or combinations thereof.

The pharmaceutical compositions also may include therapeutic and pharmaceutic agents such as, but not limited to: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which don't have the capacity to synthesize their own asparagine); antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (i.e. estrogen); Anticoaglants (heparin, synthetic heparin salts and other inhibitors of thrombin); fibrinolytic agents (such as tissue plasminogen activator, streptokinase and urokinase); antiplatelet (aspirin, dipyridamole, ticlopidine, clopidogrel, abciximab); antimigratory; antisecretory (breveldin); antiinflammatory: such as adrenocortical steroids (cortisol, cortisone, fludrocortisone, prednisone, prednisolone, 6a-methylprednisolone, triamcinolone, betamethasone, and dexamethasone), non-steroidal agents (salicylic acid derivatives i.e. aspirin; para-aminophenol derivatives i.e. acetominophen; Indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressive: (cyclosporine, tacrolimus (FK-506), sirolimus (rapamycin), azathioprine, mycophenolate mofetil); nitric oxide donors; anti-sense olgio nucleotides and combinations thereof.

The pharmaceutical compositions include any extended half-life variants of active ingredients contained therein or analogues thereof. Thus, the active ingredients can be any long acting variants of the active ingredient listed herein or analogues thereof. In some embodiments, the active ingredient includes any extended half-life or long acting variants of hGH, insulin, glucagon, glucagons-like peptide 1 (GLP-1), glucagons-like peptide 2 (GLP-2), insulin-like growth factors (IGFs). In some embodiments, the active ingredient is an extended half-life or long acting variant of hGH. Examples of extended half-life or long acting variants of hGH include, but are not limited to LB03002, NNC126-0883, NNC0195-0092, MOD-4023, ACP-001, Albutropin, somavaratan (VRS-317), and profuse GH.

With this system, the firing unit can be re-used multiple times with new cassettes to minimise the cost and environmental impact of the system, yet the complexity of providing a reusable arrangement for mixing the substances is avoided.

The firing unit is preferably attachable to the cassette only after the mixing stroke has been initiated, to minimise the risk of incorrect operation.

The cassette may comprise a release arrangement for holding the mixing element in a starting position and for releasing the mixing element to initiate the mixing stroke. The release arrangement may comprise an activating element, such as a retaining member that is engageable with the mixing element to hold the mixing element in the starting position. The retaining member may be releasable from the mixing element to initiate the mixing stroke.

Preferably, the retaining member is removable from the cassette to initiate the mixing stroke. To facilitate removal of the retaining member, the retaining member may comprise a ring pull or a grip formation, such as a tab. The retaining member may be arranged to prevent attachment of the firing unit when the retaining member is engaged with the mixing element.

The cassette may comprise a mixing spring for biasing the mixing element for movement with respect to the cassette body. The mixing spring may be a compression spring. In another arrangement, the mixing element may itself comprise a mixing spring for driving relative movement between the first and second containers.

The mixing element may be moveable in the distal direction with respect to the cassette body during the mixing stroke. For example, the mixing element may be cooperable with a stopper of the second container, and the mixing element may comprise a plunger for cooperation with the stopper. In this arrangement, distal displacement of the stopper by the mixing element causes the second substance to pass through the valve into the first chamber.

In another arrangement, the mixing element is moveable in the proximal direction with respect to the cassette body during the mixing stroke. In this case, the mixing element may cause proximal movement of the second container to cause the second substance to pass through the valve into the first chamber in response to a decrease in pressure in the first chamber.

The cassette may comprise a connecting element for attachment to the second container. The connecting element is preferably cooperable with the drive element of the firing unit. Accordingly, the connecting element may be arranged to transfer force from the drive element to the second container. The cassette may comprise a clamping arrangement for clamping the connecting element to the second container. When a mixing spring is provided for biasing the mixing element, the mixing spring may act against the connecting element.

The cassette may comprise a needle holder for holding a needle for delivery of the medicament. Preferably, the needle holder is moveable with respect to the cassette body to extend the needle from a distal end of the cassette for insertion in an injection site. With this arrangement, the needle can be automatically inserted into the injection site before delivery of the medicament. Movement of the needle holder may be driven by the drive element of the firing unit, so that extension of the needle can occur only after the firing unit has been attached to the cassette.

To prevent accidental contact with the needle after use, the cassette may comprise a shroud for shrouding the needle upon removal of the cassette from an injection site. The shroud may be biased to extend distally from the distal end of the cassette upon removal from the injection site. A locking arrangement may be provided for locking the shroud in a distally extended position after removal of the cassette from the injection site. The shroud may be biased to rotate to activate the locking arrangement.

The cassette may comprise a needle and a shield for enclosing the needle in an initial state of the cassette. The system may further comprise a cassette holder, and the shield may be attached to the cassette holder such that the shield is withdrawn from the cassette upon removal of the cassette from the cassette holder. In this way, the shield is automatically removed when the cassette is removed from the holder, and so a separate user action to remove the shield is not necessary. Conveniently, the cassette holder is arranged to hold a plurality of cassettes.

The cartridge may comprise a sealing element for closing an outlet of the first chamber. In this case, the cassette may comprise a sealing element release member for cooperation with the sealing element to open the outlet to allow delivery of the medicament. Thus the substances contained in the cartridge can remain in the sealed, sterile environment of the cartridge until the outlet is opened by the sealing element release member. To this end, the cartridge may be moveable with respect to the sealing element release member from a first position in which the outlet is closed to a second position in which the sealing element release member cooperates with the sealing element to open the outlet. The sealing element release member may cooperate with the sealing element to open the outlet after completion of the mixing stroke. For example, the cartridge may be moveable in response to movement of the drive element of the firing unit, such that the outlet remains closed until delivery of the medicament is about to occur. To maintain sterility, the cassette may include a seal arrangement for enclosing the sealing element release member when the outlet is closed.

To allow the firing unit to be securely attached to the cassette, the cassette may be provided with one or more connection formations for engagement with cooperable formations of the firing unit. Conveniently, when the system includes a cassette holder for holding a plurality of cassettes, the firing unit can be attached to a selected cassette when the cassettes are still in place on the holder.

The firing unit may include a drive spring for biasing the drive element in the distal direction. The firing unit may comprise a latch mechanism for holding the drive element in a starting position and for releasing the drive element upon operation of the trigger arrangement. In one arrangement, for example, the latch mechanism comprises a stay formation that is biased for engagement with a latching member of the drive element, and operation of the trigger arrangement displaces the stay formation against the bias to release the latching member.

The latch mechanism may be resettable to allow the firing unit to be used again. For example, when the latch mechanism comprises a stay formation, the latching member may be arranged to displace the stay formation against the bias to allow re-engagement of the latching member with the stay formation.

In the context of the present invention, the term "medicament delivery device system" encompasses an assembled medicament delivery device including components of the system as well as any arrangement of components from which a medicament delivery device can be assembled, including but not limited to a kit of parts.

The present invention also extends, in a second aspect, to a cassette for use in the system of the first aspect of the invention. The cassette may include a cartridge comprising a first container having a first chamber for storage of a first substance, a second container at least partially received in the first container and having a second chamber for storage of a second substance, and valve means for separating the first and second chambers.

In a third aspect of the invention, a firing unit for use in the system of the first aspect of the invention or with the cassette of the second aspect of the invention is provided.

In a fourth aspect, the present invention extends to a medicament delivery device comprising a cassette and a firing unit according to the second and third aspects of the invention respectively.

In a fifth aspect, a cassette set comprising a plurality of cassettes and a cassette holder for holding the cassettes is provided. Each cassette may comprise a needle and a removable shield for enclosing the needle, and each shield may be attached to the cassette holder so that removal of a cassette from the cassette holder deshields the needle.

The invention further extends, in a sixth aspect, to a method of assembling a medicament delivery device for delivery of a mixture of a first substance and a second substance, in which the first and second substances are stored in a cassette. The method comprises activating a mixing mechanism of the cassette to cause mixing of the first and second substances and, after activating the mixing mechanism, attaching a firing unit to the cassette. The method may further comprise removing the cassette from a cassette holder to deshield a needle of the cassette. Preferably, the method comprises removing an activating element from the cassette to activate the mixing mechanism.

A seventh aspect of this invention is directed to one or more of the medicaments, including one or more pharmaceutical compositions, as described above for subcutaneous injection or infusion, disposed within the medicament delivery devices described herein for the delivery of the medicament. Additionally, this invention contemplates methods of administering one or more of the medicaments, including pharmaceutical compositions, to patients with conditions susceptible to treatment with the medicaments, as well as methods of treating those conditions, by delivering the appropriate medicament using the delivery devices described herein.

Preferred and/or optional features of each aspect of the invention may be used, alone or in appropriate combination, with the other aspects of the invention also.

Embodiments of the present invention will now be described, by way of example only, with reference to the accompanying drawings, in which like reference numerals are used for like features, and in which:

FIG. 2 is a cross-sectional view of a cassette of the type shown in FIG. 1 in place on the cassette holder;

FIG. 3 is an enlarged cross-sectional view of a medicament cartridge for use in the cassette of FIG. 2;

Figure 6:
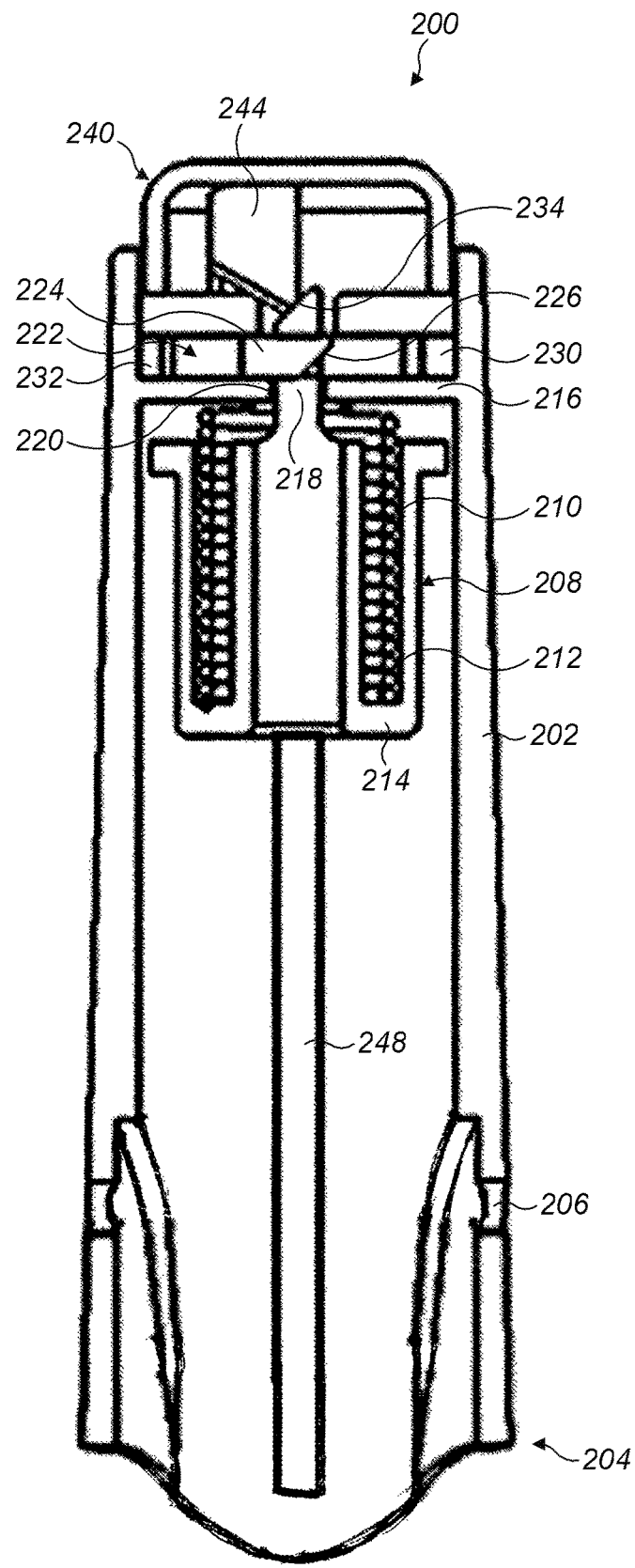
Figure 7A:
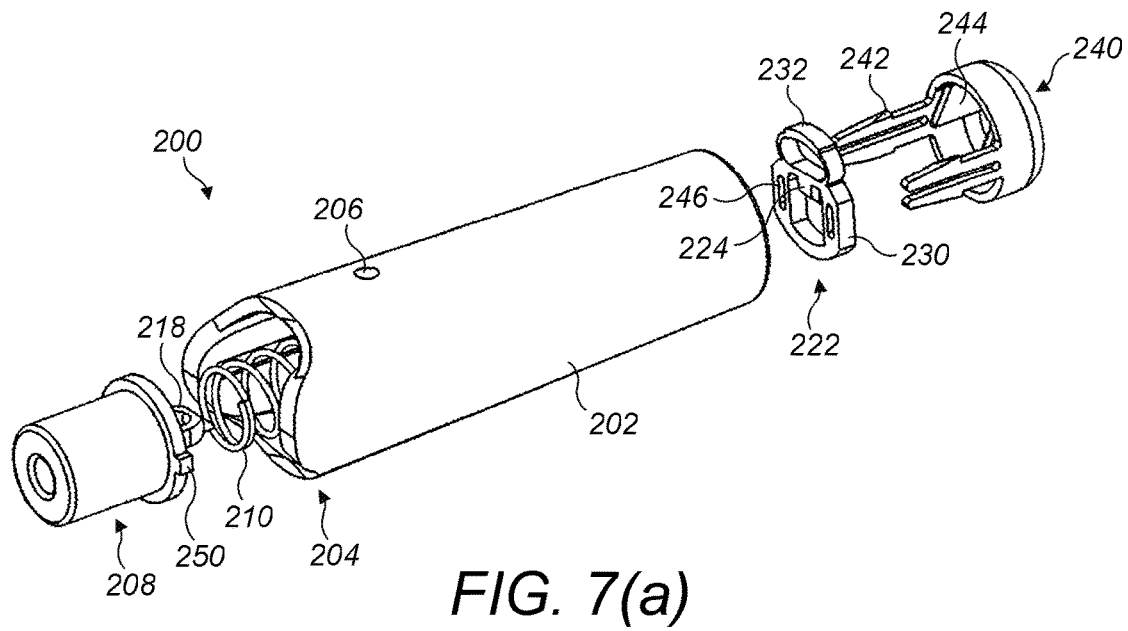
Figure 7B:
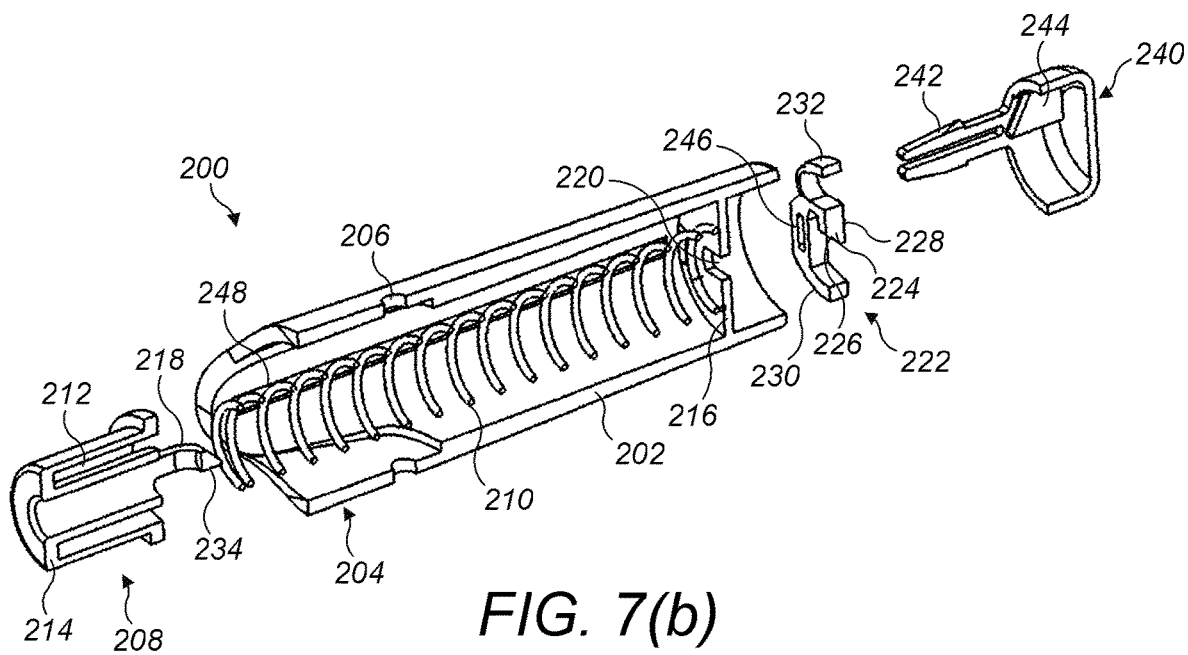
Figure 8A:
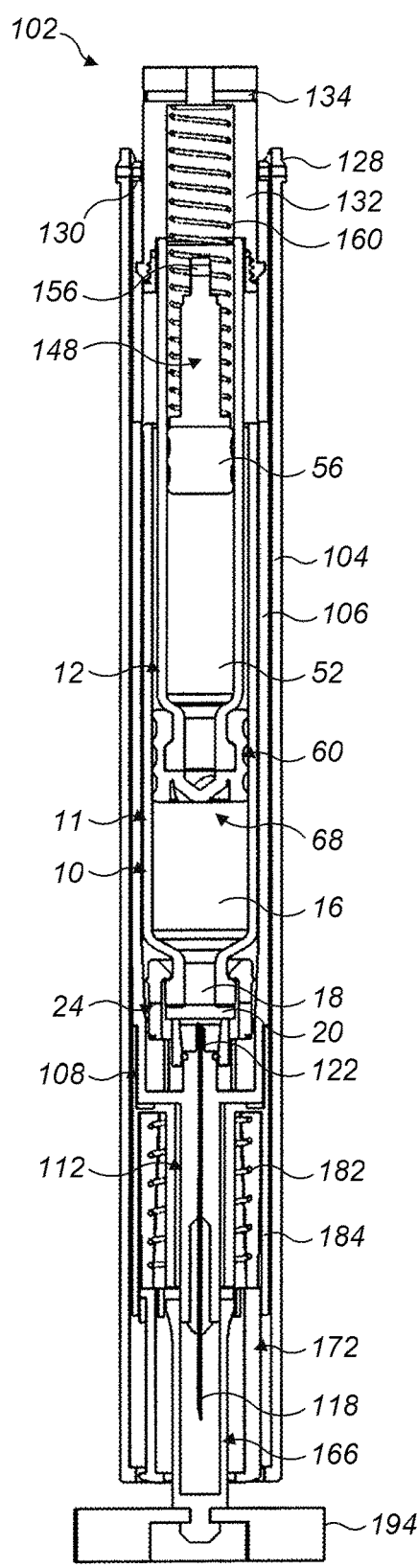
Figure 8B:
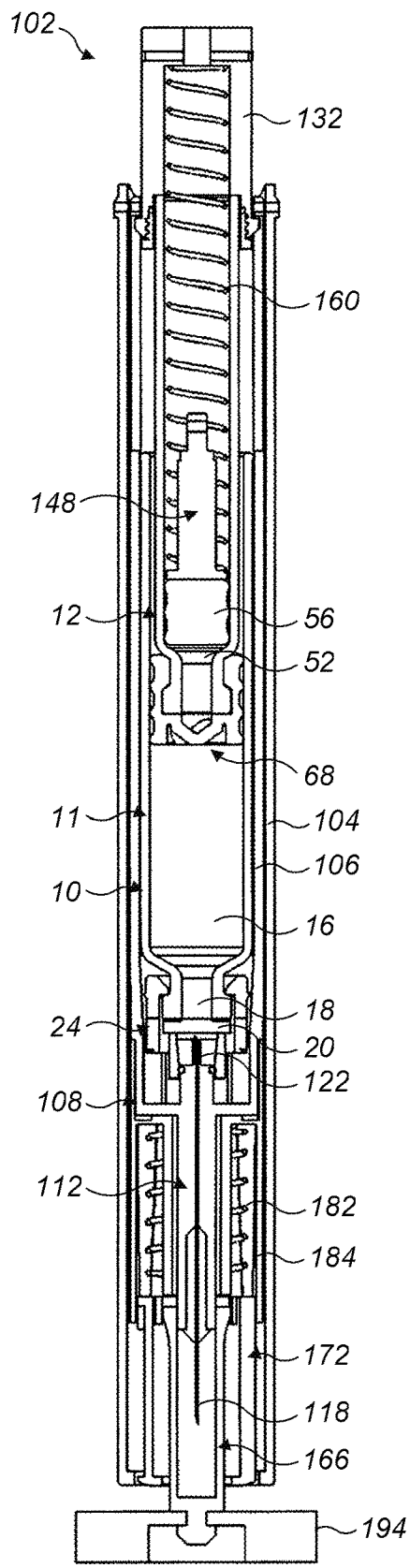
Figure 9A:
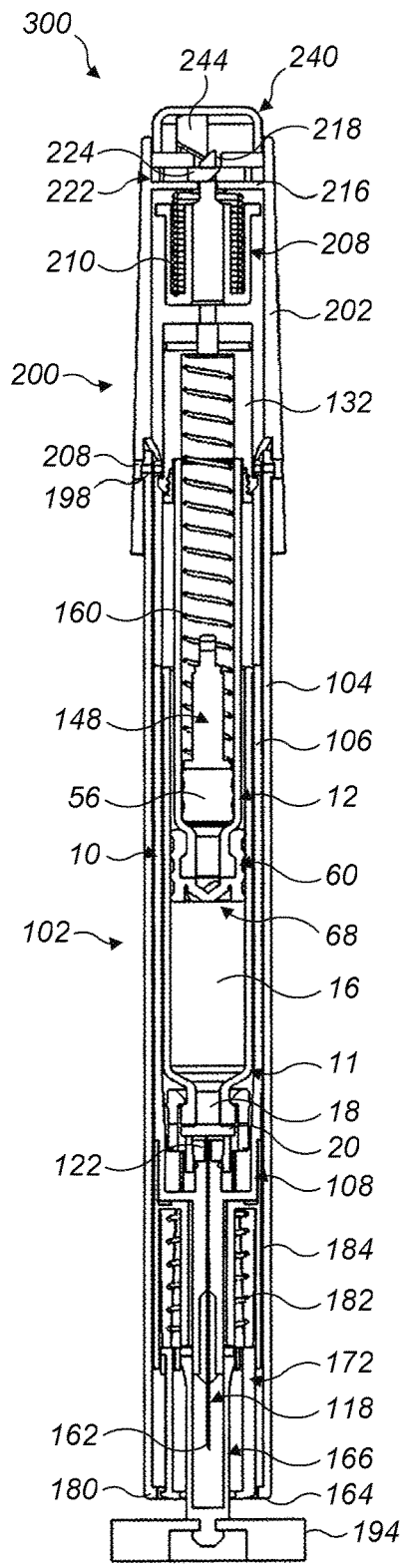
Figure 9B:
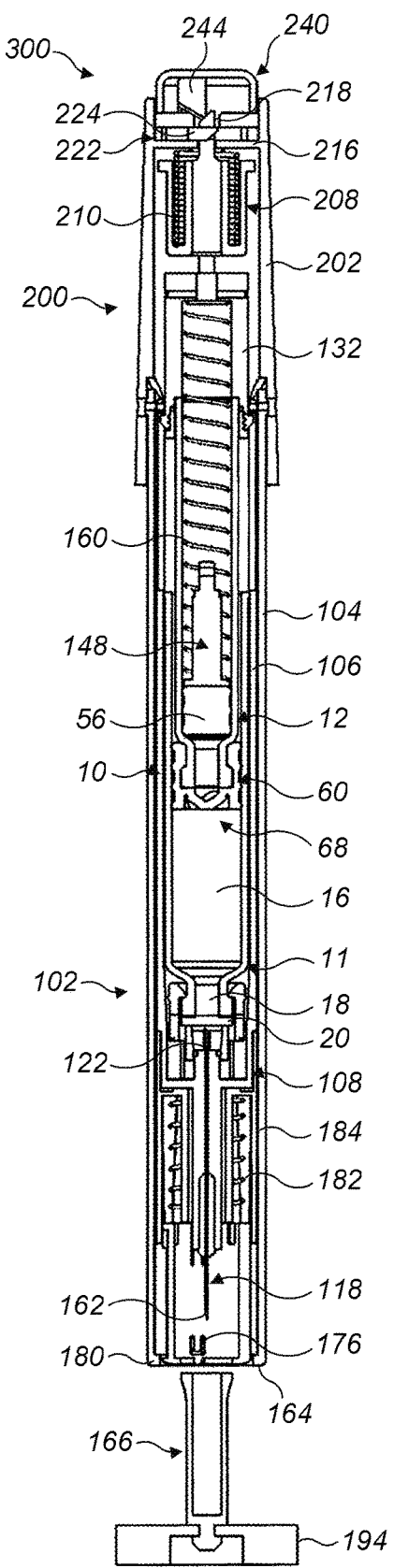
Figure 10A:
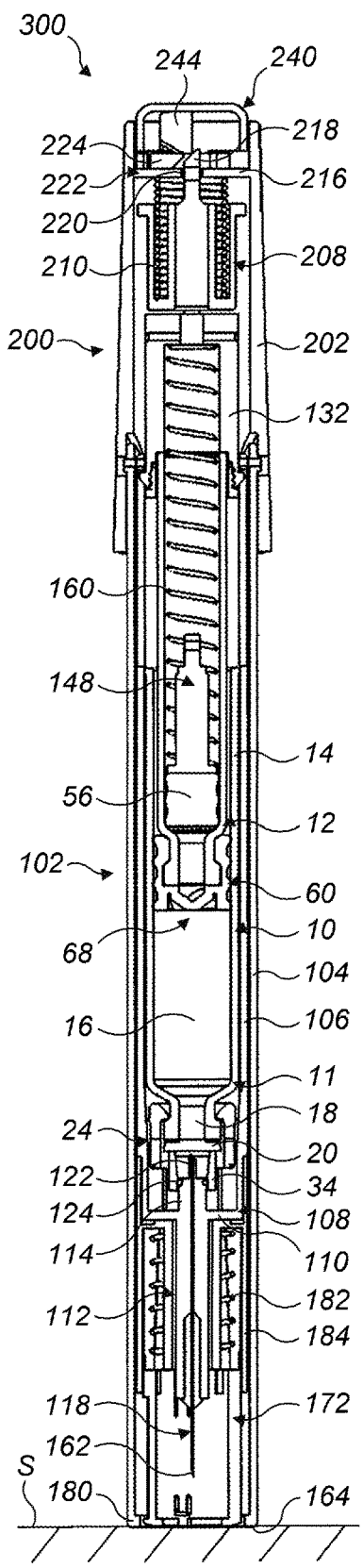
Figure 10B:
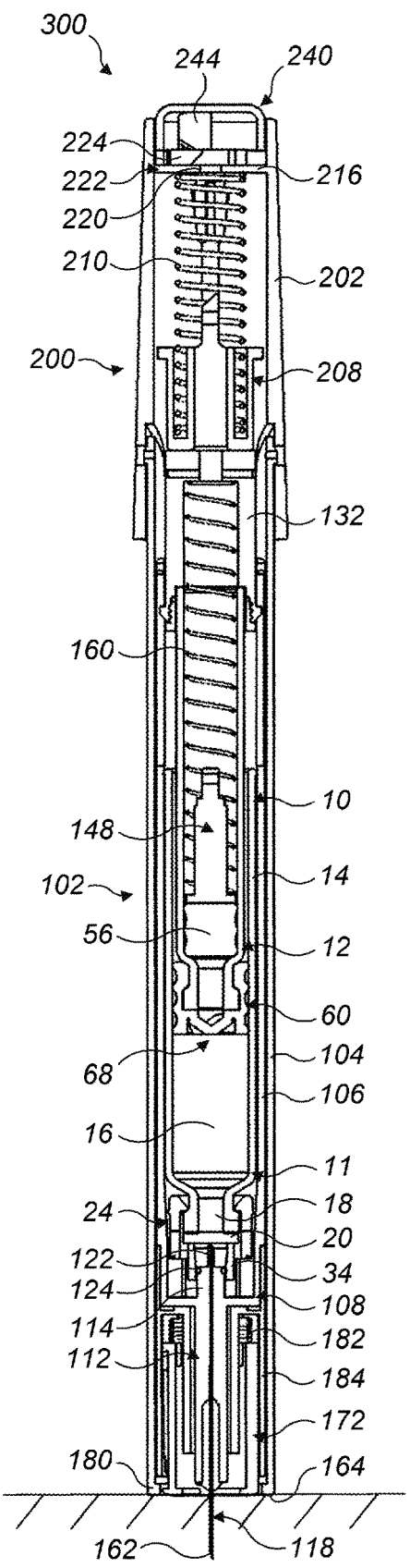
Figure 11A:
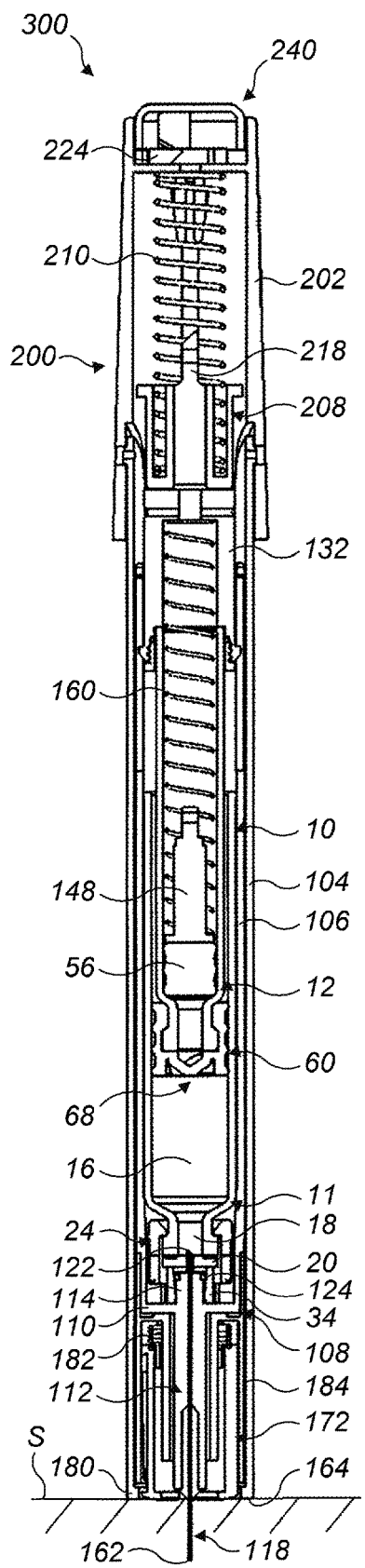
Figure 11B:
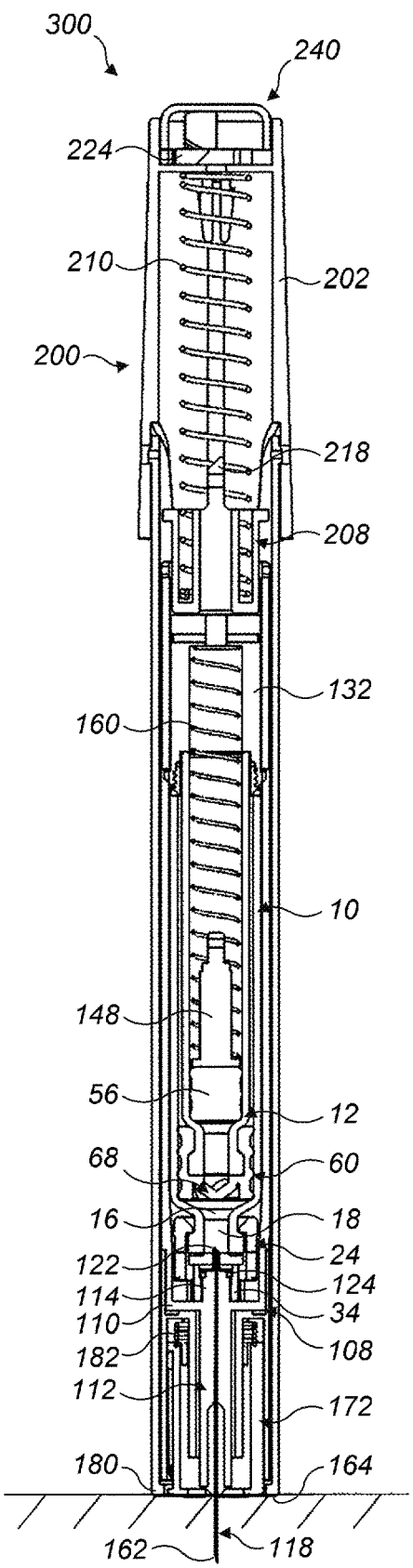
Figure 12A:
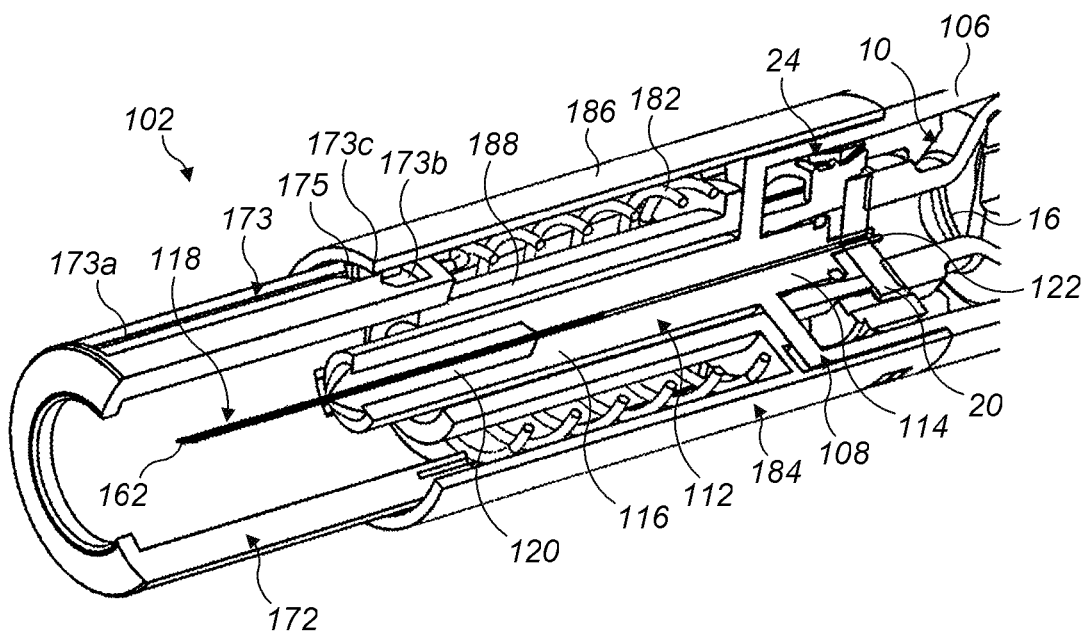
Figure 12B:
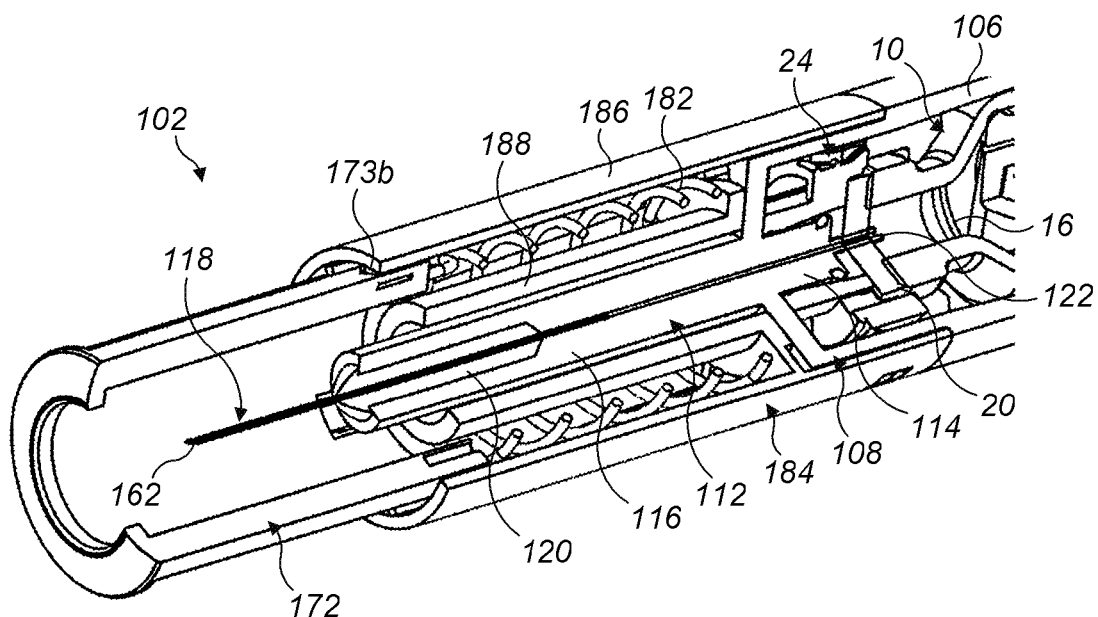
Figures 13A, 13B:
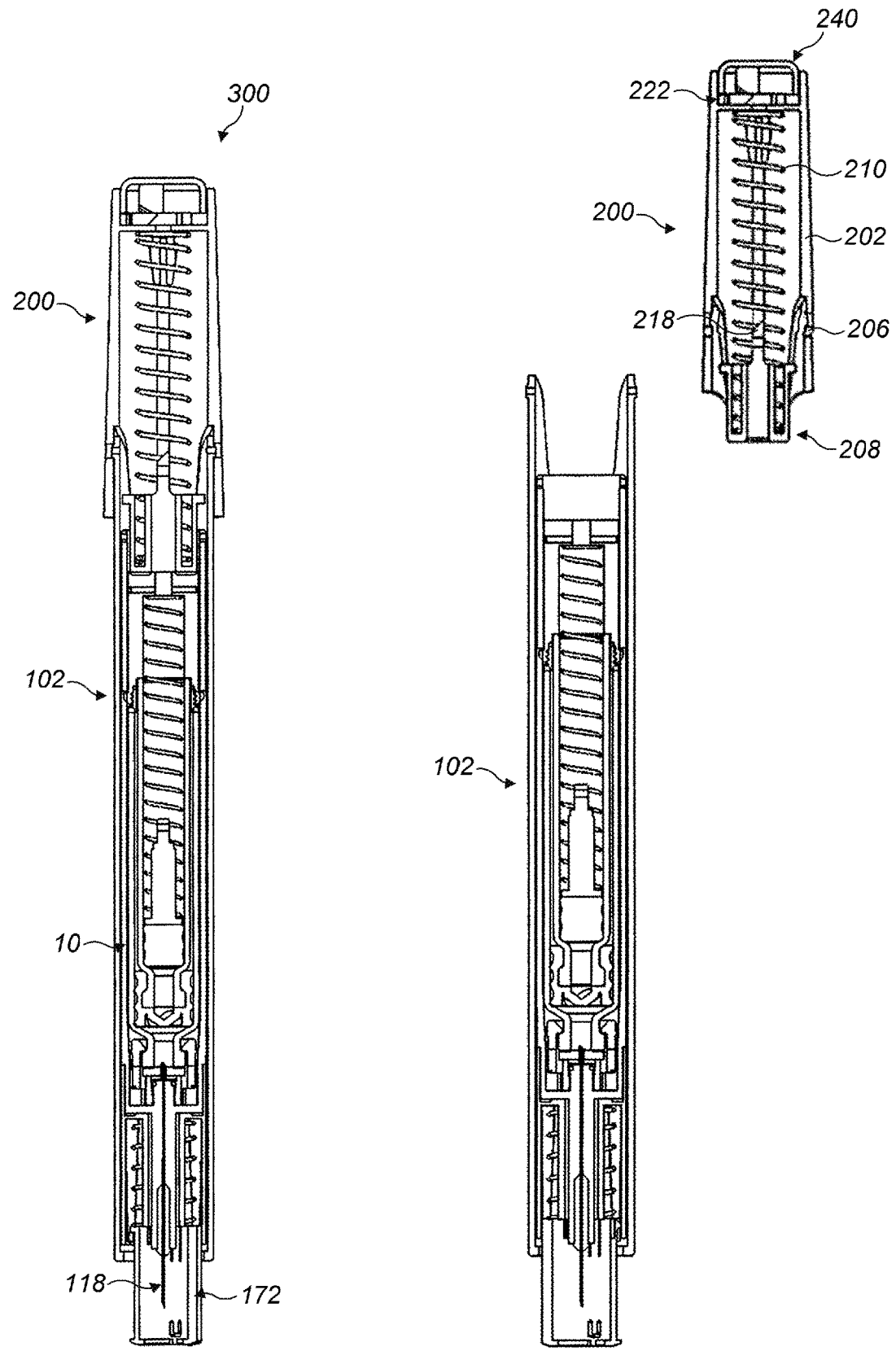

FIGS. 5(a) and 5(b) are enlarged cut-away views of the distal end of the cassette of FIG. 2 in place on the cassette holder;

FIG. 6 is a cross-sectional view of a firing unit for use in the delivery device of the present invention;

FIGS. 7(a) and 7(b) are exploded isometric and cut-away views of the firing unit of FIG. 6, respectively;

FIGS. 8(a) and 8(b) are cross-sectional views of the cassette of FIG. 2 at different states during a mixing stroke of the cassette;

FIGS. 9(a) and 9(b) are cross-sectional views of a delivery device comprising the cassette of FIG. 2 and the firing unit of FIG. 6, when attached to and removed from the cassette holder respectively;

FIGS. 10(a) and 10(b) are cross-sectional views of the delivery device of FIG. 9(b) in place on an injection site, before and after activation of the firing unit, respectively;

FIGS. 11(a) and 11(b) are cross-sectional views of the delivery device of FIG. 9(b), showing successive stages in a delivery stroke of the device;

FIGS. 12(a) and 12(b) are enlarged cut-away views of the distal end of the delivery device of FIG. 9(b) showing successive stages in deployment of a shroud component, with a cassette body component omitted for clarity; and FIGS. 13(a) and 13(b) are cross-sectional views of the delivery device of FIG. 9(b) at the end of the delivery stroke and after disassembly of the device, respectively.

Figure 1:
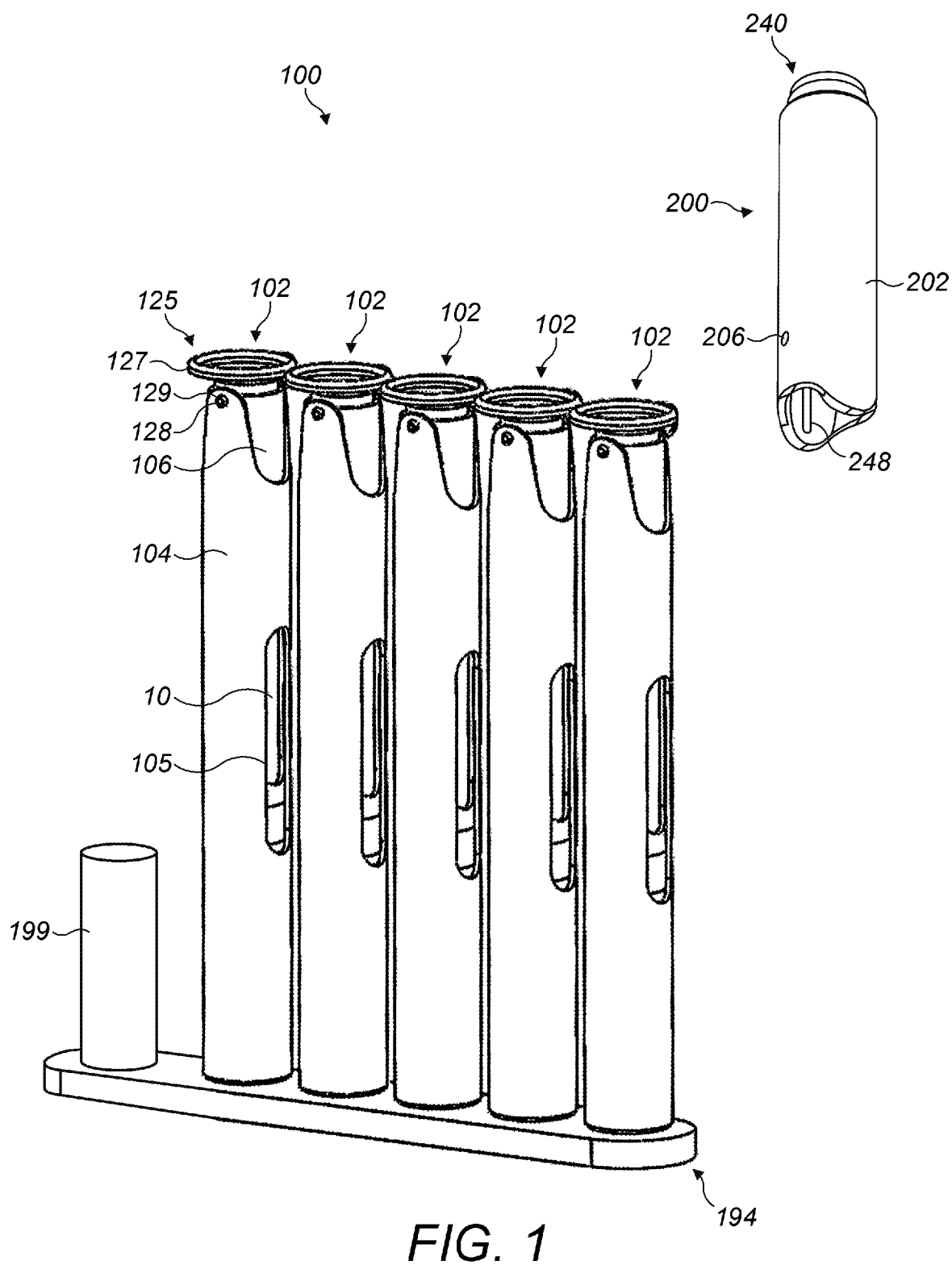
FIG. 1 is an isometric view of a set of cassettes, a cassette holder and a firing unit for use in a delivery device system according to the present invention.

A medicament delivery device system 100 according to an embodiment of the present invention is shown in FIG. 1. The system 100 includes a set of medicament cassettes 102 which are stored on a cassette holder 194, and a firing unit 200. The cassettes 102 are intended for disposal after a single use, whereas the firing unit 200 is reusable. To this end, the cassettes 102 are removably attachable to the firing unit 200.

Referring also to FIG. 2, which is a cross-sectional view of one of the cassettes 102 mounted on the holder 194, each cassette 102 includes a generally tubular body 104 that receives a medicament cartridge 10. A window 105 (see FIG. 1) in the body 104 is provided so that the internal components of the cassette 102 can be viewed in operation. A tubular chassis 106 is slidably received in the cassette body 104 and is arranged concentrically between the cartridge 10 and the cassette body 104. Although not clearly shown in the figures, the chassis 106 also includes a window to allow the cartridge 10 to be seen through the window 105 of the cassette body 104 in use.

The cartridge 10, which is shown in isolation in FIG. 3, comprises a first or outer container 11 and a second or inner container 12 that is telescopably received in the proximal end of the outer container 11. The outer container 11 comprises a generally tubular body 14 which defines a first chamber 16 for containing a first substance. A first, distal end of the body 14 (lowermost in FIGS. 2 and 3) defines an outlet 18 of the first chamber 16 that is closed by a closure member in the form of an elastomeric disc or septum 20, which seals against the end face of a reduced-diameter neck 22 of the body 12.

The septum 20 is held in place by a coupling element 24 that is in clipped engagement with a collar 26 on the neck 22 of the body 12, by way of clip formations 28. The clip formations 28 are disposed at the ends of a plurality of legs 30 that extend proximally from a ring part 32 of the coupling element 24.

The ring part 32 supports a tubular throat 34 of the coupling element 22. The throat 34 is integrally formed with the coupling element 24, and defines a generally frustoconical bore 36. An inner end of the throat 34 presses against the septum 20 to seal the septum 20 against the end of the neck 22. The circumference of the throat 34 is uninterrupted so that a sealing force is applied to the septum 20 around a complete circle. An annular groove 38 is disposed on the inside of the bore 36 adjacent to the distal end of the throat 34.

The proximal end of the first chamber 16 is closed by the inner container 12. The inner container 12 comprises a generally tubular body 50 which defines a second chamber 52 for containing a second substance. The inner container body 50 is similar in shape and construction to the outer container body 14, and thus comprises a neck 54 and a collar 55 that extends around the neck 54 at its distal end.

An elastomeric bung or stopper 56 is received in the outer container body 50 to close the proximal end of the second chamber 52. The distal end of the inner container body 50 is closed by a second or inner closure member in the form of a cap 60 that fits over the collar 55.

The cap 60 is formed from an elastomeric material, such as a halobutyl or other rubber material, and comprises an end face 62 and an annular ring part 64 that extends proximally from the end face 62 to receive the neck 54 of the inner container body 50. The ring part 64 is shaped to engage around and form a seal against the neck 54 on the proximal side of the collar 55 to secure the cap 60 to the inner container body 50. The cap 60 has an outer diameter that is sized so that a seal is formed between the cap 60 and the inner wall of the outer container body 14. To enhance the seal, a plurality of ridges 66 are formed on the outer surface of the cap 60.

The distal face 62 of the cap 60 is formed to provide a one-way slit valve 68 for closing the distal end of the second chamber 52. To this end, the distal face 62 comprises a generally wedge-shaped region 70 that faces distally away from the second chamber 52, and a slit extends through the cap 60 along the ridge to divide the wedge-shaped region 70 into a pair of valve members 72. The valve members 72 are biased towards one another so that, when fluid pressures on each side of the slit valve 68 are equal, the valve members 72 seal against one another to close the slit. When the pressure on the proximal side of the slit valve 68 is sufficiently greater than the pressure on the distal side, the bias of the valve members 72 can be overcome to allow fluid flow through the slit valve 68 in the distal direction. However, when the pressure on the distal side of the slit valve 68 exceeds the pressure on the proximal side, the valve 68 closes.

The coupling element 24 is cooperable with a hub part 108 of the chassis 106. The hub part 108 comprises a disc-shaped support 110 that supports a tubular needle holder 112. A relatively short part 114 of the needle holder 112 extends proximally from the support 110 towards the coupling element 24, and a relatively long part 116 of the needle holder 112 extends distally from the support 110. A hypodermic needle 118 is mounted in the needle holder 112 and is retained by a sealing material 120.

A tubular piercing member 122 extends towards the cartridge 10 from the proximal part 114 of the needle holder 112. The bore of the piercing member 122 is fluidly connected to the lumen of the needle 118 by the bore of the needle holder 112. In an initial state of the cassette 102, as shown in FIG. 2, the coupling element 24 of the cartridge 10 and the hub part 108 of the chassis 106 are positioned relative to one another in a first attachment position, in which the piercing member 122 is spaced from the septum 20 of the cartridge 10 so that the septum 20 remains intact and the outlet 18 of the cartridge 10 remains closed.

An O-ring 124 is retained in an annular groove on the outside of the proximal part 114 of the needle holder 112. In the initial state of the cassette 102, with the cartridge 10 and the chassis 106 in the first attachment position, the O-ring 124 locates in the annular groove 38 of the throat 34 of the coupling element 24 to form a seal between the needle holder 112 and the coupling element 22. The piercing member 122 is therefore kept sterile in an enclosed chamber on the distal side of the septum 16.

Figure 4:
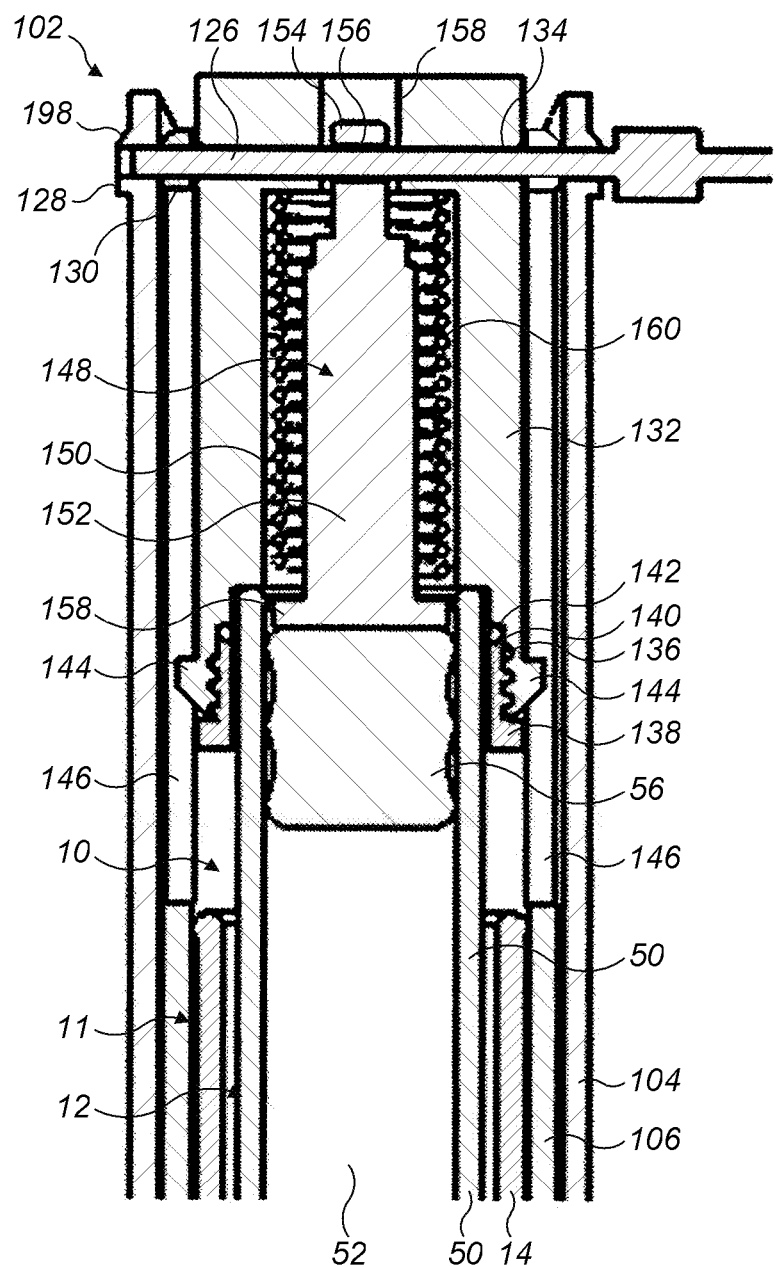
FIG. 4 is an enlarged cross-sectional view of a proximal end of the cassette of FIG. 2.

In the initial state of the cassette 102, the cartridge 10 and the chassis 106 are fixed in position relative to one another and to the cassette body 104 by a retaining member comprising a ring pull component 125. Referring to FIG. 4, which is an enlarged view of the proximal end of the cassette 102, the ring pull component 125 comprises a retaining pin 126 that is connected at one end to a ring 127 by way of a flexible tie 129. The retaining pin 126 passes through the cassette body 104 and is engaged by a pair of diametrically opposed holes 128 formed in the cassette body 104 adjacent to its proximal end. The retaining pin 126 also passes through a further pair of diametrically opposed holes 130 formed in the chassis 106 to lock the chassis 106 to the cassette body 104.

The inner container 12 of the cartridge 10 is attached to a connector element 132. The connector element 132 is generally tubular and includes a diametrically-extending bore 134 adjacent to its proximal end. In the initial state of the cassette 102, the bore 134 is aligned with the holes 128, 130 in the cassette body 104 and the chassis 106, and the retaining pin 126 extends through the bore 134 to lock the connector element 132 in position with respect to the chassis 106 and the cassette body 104.

A clamping arrangement is provided to secure the connector element 132 to the inner container body 50. A distal end region 136 of the connector element 132 has an enlarged internal diameter to accept the proximal end of the inner container body 50, and is internally threaded to mate with an externally-threaded part of a clamping collar 138. The clamping collar 138 is disposed annularly around the inner container body 50. A clamping ring 140, comprising an elastomeric O-ring, is also disposed around the inner container body 50 and is retained between the proximal end of the clamping collar 138 and a shoulder 142 formed in the bore of the connector element 132. During assembly of the cassette 102, the clamping collar 138 can be turned with respect to the connector element 132 to squeeze the clamping ring 140 against the outer wall of the inner container body 50. The radial clamping force thus applied by the clamping ring 140 to the inner container body 50 locks the second container body 50 to the connector element 132.

The position of the inner container 12 with respect to the cassette body 104 and the chassis 106, and therefore the position of the cartridge 10 with respect to the hub part 108, is maintained while the retaining pin 126 is engaged with the connector element 132.

A pair of radially-extending clips 144 is provided on the outer surface of the distal end region 136 of the connector element 132. The clips 144 engage with longitudinally-extending slots 146 formed in the chassis 106 to guide the connector element 132 for axial movement with respect to the chassis 106 during operation, as will be explained in more detail below.

A mixing element 148, in the form of a plunger, is received in an axial cavity 150 of the connector element 132. The mixing element 148 includes a shaft 152 that has a reduced-diameter proximal end region 154 having a diametrically-extending bore 156. In the initial state of the cassette 102, the proximal end region 154 extends into a reduced-diameter axial bore 158 of the connector element 132 that opens to the proximal end of the axial cavity 150. When in the initial state, the retaining pin 126 extends through the diametrically-extending bore 156, therefore locking the mixing element 148 in position with respect to the cassette body 104, the chassis 106, and the connector element 132.

The mixing element 148 also includes, at the distal end of the shaft 152, an enlarged diameter head 158. The head 158 is arranged to cooperate with the stopper 56 of the cartridge 10 during operation, as will be explained further below.

A mixing spring 160, in the form of a compression spring, is disposed between the head 158 of the mixing element 148 and the proximal end of the axial cavity 150. The mixing spring 160 acts as a biasing means to bias the mixing element 148 in the distal direction with respect to the connector element 132. When the retaining pin 126 in place in the initial state of the cassette 102, the mixing spring 160 is compressed and the retaining pin 126 holds the mixing element 148 against the bias of the mixing spring 160.

Referring back to FIG. 2, and additionally to FIGS. 5(*a*) and 5(*b*) which are enlarged views of the distal end of the cassette 102 cut away on different planes, a distal part 162 of the needle 118 projects distally from the needle holder 112 towards the open distal end 164 of the cassette body 104. In the initial state of the cassette 102, the tip of the needle 118 is retracted with respect to the distal end 164 of the cassette body 104.

A needle shield 166 is provided to enclose the distal part 162 of the needle 118. The needle shield 166 comprises a bore 168 for receiving the distal part 162 of the needle 118. The bore 168 is closed at its distal end 170 so that the distal part 162 of the needle 118 remains sterile within the bore 168 until the needle shield 166 is removed.

It will be appreciated that, with the needle shield 166 in place and with a seal formed between the coupling element 24 and the needle holder 112 in the initial state of the cassette 102, the sterility of all of the components that are subsequently able to come into contact with the medicament and the injection site (including the piercing member 122 and the distal part 162 of the needle 118) can be maintained.

A generally tubular shroud 172 is arranged concentrically between the needle shield 166 and the cassette body 104. In the initial state of the device cassette 102, the shroud 172 is also retracted with respect to the distal end 164 of the cassette body 104.

As seen most clearly in FIG. 5(a), an outwardly-facing ridge formation 174 is disposed on a resilient arm 176 that is formed in the wall of the shroud 172. The needle shield 166 is provided with a longitudinal rib 178 that braces the arm 176 to prevent inward deflection of the arm 176 when the needle shield 166 is in place. The ridge formation 174 is arranged to cooperate with an inwardly-directed collar 180 disposed at the distal end 164 of the cassette body 104 to prevent distal movement of the shroud 172 with respect to the cassette body 104 during removal of the needle shield 166.

Referring back to FIG. 2, the shroud 172 is biased in the distal direction with respect to the chassis 106 by a lockout spring 182. The lockout spring 182 is a helical spring that acts in both compression and torsion, so that a torsional bias is also applied between the shroud 172 and the chassis 106. The distal end of the lockout spring 182 is engaged with the shroud 172 so as to allow torsion to be transferred to the shroud 172. The proximal end of the lockout spring 182 is similarly engaged with a spring guide 184 that is clipped to the distal end of the chassis 106. The spring guide 184 has an outer tubular part 186 having an outer diameter that is substantially the same as the outer diameter of the chassis 106, and an inner tubular part 188 that extends distally from the hub part 108 of the chassis 106 in a concentric arrangement with the distal part 116 of the needle holder 112.

In the initial state of the cassette 102, the lockout spring 182 is substantially relaxed or extended in the axial direction, so that a relatively low axial force is applied to the shroud 172 by the spring 182. Referring again to FIGS. 5(a) and 5(b), adjacent to the proximal end of the shroud 172, a plurality of stops 190 (only one of which is shown) are provided on the outer surface of the shroud 172 to cooperate with the distal end of the outer part 186 of the spring guide 184, to guard against unintended movement of the shroud 172 with respect to the chassis 106. Rotation of the shroud 172 is prevented by engagement of the longitudinal rib 178 of the needle shield 166 with a slot 191 formed on the inner wall of the shroud 172 (see FIG. 5(a)). A plurality of clips 192 (one of which is visible in FIG. 5(b)) are also provided at the proximal end of the shroud 172. The clips 192 are biased to bear against the inner surface of the outer part 186 of the spring guide 184 to reduce or prevent movement of the shroud 172 within the cassette 102 and to prevent the shroud 172 from being driven out of the housing 104.

The cassette holder 194 comprises a base plate having a plurality of apertures 195. Each aperture 195 is arranged to accept a push clip 196 disposed on the distal end of the needle shield 166 of a respective cassette 102. The apertures 195 are disposed above a recessed channel 197 in the underside of the holder 194 that accommodates the push clips 196. The push clips 196 and apertures 195 are shaped and dimensioned so that, once a push clip 196 has been inserted into the aperture 195 to connect a cassette 102 to the holder 194, the needle shield 166 of the cassette 102 is not subsequently readily releasable from the holder 194.

The cassettes 102 are suitably spaced along the cassette holder 194 to allow the firing unit 200 to be attached to a cassette 102 while the cassettes 102 are still attached to the holder 194. Each cassette 102 includes a pair of outwardly-facing connector clips 198 for cooperation with the firing unit 200. As best seen in FIG. 4, the connector clips 198 are formed at the locations of the holes 128 in the proximal end of the cassette housing 104.

Referring now to FIG. 6, which is a cross-section through the firing unit 200, and to the exploded views of FIGS. 7(a) and 7(b), the firing unit 200 of the delivery device system 100 takes the form of an elongate cap that can be fitted over the proximal end of a cassette 102. Each firing unit 200 comprises a generally tubular firing unit body 202 having a distal end region 204 that is shaped in a complementary way to the proximal end of the cassette housing 104. A pair of diametrically-opposed apertures 206 are provided in the distal end region 204 of the firing unit body 202 to accommodate the connector clips 198 of a cassette 102.

The firing unit 200 houses a generally tubular delivery drive element 208 that is biased in the distal direction with respect to the firing unit body 202 by a delivery spring 210, which in this example is a compression spring. A distal part of the delivery spring 210 is accommodated in an annular cavity 212 that extends distally into the delivery drive element 208. The distal end of the delivery spring 210 bears against a distal end wall 214 of the cavity 212. The proximal end of the delivery spring 210 bears against a bridge part 216 of the firing unit body 202 that extends across its diameter.

A loop-shaped latching member 218 extends proximally from the delivery drive element 208. In an initial state of the firing unit 200 (as shown in FIG. 6), the latching member 218 extends through an aperture 220 in the bridge part 216 to engage with a latch component 222. As can be best seen in FIGS. 7(a) and 7(b), the latch component 222 comprises a stay formation 224 having a ramped distal face 226 and a flat proximal face 228. The stay formation 224 projects inwardly from one side of a support ring 230. A latch spring 232 is provided on the outside of the support ring 230, adjacent to the stay formation 224. The latch spring 232 is in the form of a resilient loop of material that is formed integrally with the support ring 230.

Referring back to FIG. 6, the latch spring 232 biases the latch component 222 against the opposite wall of the firing unit body 202 so that, in the initial state of the firing unit 200, the stay formation 224 is aligned with the aperture 220 in the bridge part 216. During assembly of the firing unit 200 (and subsequently when the firing unit 200 is re-set), the delivery drive element 208 can be moved proximally with respect to the firing unit body 202 so that the latching member 218 passes through the aperture 220. The latching member 218 has a ramped proximal face 234 that cooperates with the ramped distal face 226 of the stay formation 224 to move the latch component 222 laterally with respect to the firing unit body 202, allowing the latching member 218 to pass the stay formation 224 and deforming the latch spring 232. The latch component 222 then moves back under the influence of the latch spring 232, so that the stay formation 224 extends through the latching member 218 to prevent movement of the latching member 218, and therefore the delivery drive element 208, in the distal direction with respect to the firing unit body 202.

A trigger button 240 is disposed at the proximal end of the firing unit 200. As shown most clearly in FIG. 7(b), the trigger button 240 includes two pairs of distally-extending arms 242 that extend through respective slots (not clearly shown) in the bridge part 216 of the firing unit body 202. Each pair of arms 242 is shaped to flex toward one another to pass through a respective slot during assembly of the firing unit 200 and then to spring apart to retain the trigger button 240 in place on the firing unit body 202. The trigger button 240 includes, on its distal side, a pair of distally-extending, wedge-shaped release pins 244. The release pins 244 are positioned to engage with respective slots 246 in the latch component 222 when the trigger button 240 is moved in the distal direction with respect to the firing unit body 202, to cause displacement of the latch component 222 laterally against the bias of the latch spring 232, as will be described in more detail below.

The delivery drive element 208 is guided for axial movement with respect to the firing unit body 202 by a pair of longitudinally-extending channels 248 (one of which can be seen in each of FIGS. 6 and 7(b)) formed in the inside wall of the firing unit body 202. The delivery drive element 208 is provided with a pair of radially-projecting ribs 250 (see FIG. 7(a)) for engagement with the channels 248.

A sequence of steps for the injection of a medicament from the delivery device system 100 will now be described.

An initial set of steps takes place with the cassette 102 still attached to the cassette holder 194. The set of cassettes 102 would be supplied with the ring 127 of each ring pull component 125 stowed on the proximal end of the respective cassette, as shown in FIG. 1, optionally with the rings 127 held in place by a packaging part, clip, label or other feature.

The user first pulls the ring 127 off the distal end of a selected cassette 102 to extend the ring pull component 125 laterally, as shown in FIG. 2. The ring pull component 125 can then be pulled to withdraw the retaining pin 126 from the cassette 102 to initiate a mixing stroke of the cassette 102.

When the retaining pin 126 is withdrawn, the mixing element 148, the connector element 132, the chassis 106 and the cassette body 104 all become free to move with respect to one another along the axis of the cassette 102. During the mixing stroke, the cassette body 104 and the chassis 106 remain stationary with respect to the cassette holder 194, and the hub part 108 of the chassis 106 remains in the first attachment position relative to the coupling element 24 of the cartridge 10, with the septum 20 intact.

However, upon withdrawal of the retaining pin 126, the mixing element 148 is released from the connector element 132 and moves distally under the force of the mixing spring 160 to displace the stopper 56 of the cartridge 10 towards the distal end of the inner container 12, as shown in FIG. 8(a). This causes the second substance to flow through the valve 68 from the second chamber 52 into the first chamber 16 to mix with the first substance. Because the outlet 18 of the first chamber 16 is closed by the septum 20, the increase in volume in the first chamber 16 causes the inner container 12 to move proximally with respect to the cassette body 104, so that the connector element 132 emerges from the proximal end of the cassette 102. FIG. 8(b) shows the cassette 102 at the end of the mixing stroke, when the stopper 56 has reached the distal end of the second chamber 52. At this point, the pressure in the first and second chambers 16, 52 equalises and the valve 68 closes.

The emergence of the connector element 132 indicates to the user that the mixing stroke has been performed. The firing unit 200 can then be attached to the cassette 102. It will be appreciated that the firing unit 200 cannot be attached to the cassette 102 while the ring pull component 125 is still in place, which advantageously prevents use of a cassette 102 before the mixing stroke has been initiated.

FIG. 9(a) shows the firing unit 200 in position and engaged with the proximal end of the cassette 102 to form an assembled delivery device 300, with the connector clips 198 engaged in the apertures 206 of the firing unit body 202. At this stage, the distal end of the drive element of the firing unit 200 is spaced from the proximal end of the connector element 132 of the cassette 102.

The device 300, including the cassette 102 and the attached firing unit 200, are then removed from the cassette holder 194. Referring to FIG. 9(b), the needle shield 166 remains attached to the cassette holder 194, so that the distal end 162 of the needle 118 is deshielded as the cassette 102 is removed from the cassette holder 194. As described above with reference to FIG. 5(a), engagement of the ribs 174 (not visible in FIG. 9) of the shroud 172 with the collar 180 of the cassette body 104 stop the shroud 172 from moving distally with respect to the cassette body 104 as the needle shield 166 is withdrawn from the cassette 102. In turn, the stops 190 (not visible in FIG. 9) prevent the spring guide 184, and therefore the chassis 106, the hub part 108 and the needle 118, from moving distally with respect to the cassette body 104 during removal of the cassette 102 from the holder 194.

After removal from the holder 194, the distal end 164 of the cassette 102 can be placed against an injection site S, as shown in FIG. 10(a). The trigger button 240 of the firing unit 200 can then be pressed in the distal direction. As explained above with reference to FIGS. 6 and 7, the release pins 244 of the trigger button 240 cooperate with the latch component 222 to move the stay formation 224 laterally with respect to the firing unit body 202 (to the left in FIG. 10). The stay formation 224 thus disengages from the latching member 218 of the delivery drive element 208.

FIG. 10(a) shows the device 300 immediately after disengagement of the stay formation 224 from the latching member 218. The latching member 218 can move distally through the aperture 220 in the bridge part 216 of the firing unit body 202, allowing the drive element 208 to move distally with respect to the firing unit body 202 under the influence of the drive spring 210 to perform a delivery stroke of the device 300.

Upon movement of the drive element 208, the distal end of the drive element 208 comes into contact with the proximal end of the connector element 132. The connector element 132 acts to transfer the force of the drive spring 210 from the drive element 208 to the inner container 12 of the cartridge 10. Thus the inner container 12 is moved distally with respect to the cassette body 104. Because the valve 68 in the cap 60 is closed, the inner container 12 now acts as a moveable piston or plunger for the outer container 11.

Due to the friction between the cap 60 and the outer container body 14, the outer container 11 moves distally together with the inner container 12 during an initial part of the movement of the inner container 12. This distal movement of the outer container 11 drives the hub 108 distally, which causes the distal part 162 of the needle 118 to extend out of the device 300 to pierce the injection site S, as shown in FIG. 10(b). The chassis 106 and the spring guide 184 move distally with the hub part 108, so that the spring guide 184 pushes past the stops 190 of the shroud 172 (see FIG. 5), and so that the lockout spring 182 becomes compressed against the proximal end of the shroud 172.

Distal movement of the needle 118 continues until the distal end of the spring guide 184 contacts the collar 180 at the distal end 164 of the cassette body 104 to block further travel of the spring guide 184, the chassis 106 and the hub part 108.

Now, upon continued distal movement of the inner container 12 in the delivery stroke, the outer container 11 moves distally with respect to the chassis 106, to move the coupling element 24 and the hub part 108 of the chassis 106 into a second attachment position relative to one another. Referring to FIG. 11(a), in the second attachment position, the piercing member 122 pierces the septum 20 to open the outlet 18 of the first chamber 16 of the cartridge 10 and to establish a fluid connection pathway from the first chamber 16 to the needle 118. The throat 34 of the coupling element 24 of the cartridge 10 moves distally with respect to the distal part 114 of the needle holder 112, so that the sealing ring 124 moves out of engagement with the throat 34.

Movement of the outer container 11 with respect to the chassis 106 stops when the distal end of the throat 34 contacts the support 110 of the hub part 108. Subsequently, the delivery stroke continues with movement of the inner container 12 in the distal direction with respect to the outer container 11. The cap 60 of the inner container 12, with the closed valve 68, thus forces the mixture of the first and second substances from the first chamber 16 through the needle 118 for delivery into the injection site S. FIG. 11(b) shows the device 300 at the end of the delivery stroke, when the cap 60 has reached the distal end of the first chamber 16.

Once the delivery stroke is complete, the device 300 can be removed from the injection site S. As the device 300 is removed, the shroud 172 is deployed from the distal end 164 of the cassette body 104 due to the action of the lockout spring 182. The shroud 172 therefore conceals the needle 118 as it is withdrawn from the injection site S.

As will now be explained with reference to FIG. 12, the shroud 172 is arranged to lock in its distally-extended position, to prevent accidental contact with the needle 118 after use of the device.

FIG. 12(a) is a cut-away view of the distal end of the cassette 102, with the cassette body 104 omitted, showing the shroud 172 when it has just reached the furthest distal extent of its travel. The shroud 172 is provided with a channel or keyway 173 for guiding movement of the shroud 172 with respect to the spring guide 184. An inwardly-directed projection or key 175 is provided at the distal end of the outer tubular part 186 of the spring guide 184 for cooperation with the keyway 173.

The keyway is generally J-shaped, and includes a relatively long guide portion 173a that extends longitudinally along the shroud 172 and a recess 173b that is disposed parallel to the first portion 173a and connected to the first portion 173a at the proximal end of the keyway 173. When the shroud 172 is first deployed during removal from the injection site, key 175 cooperates with the first portion 173a of the keyway 173 to prevent rotation of the shroud 172 with respect to the spring guide 184. Distal movement of the shroud 172 can continue until the proximal end of the keyway 173 reaches the key 175. At this point, the shroud 172 can rotate under the torsional bias applied to by the lockout spring 182, to bring the key 175 into the recess 173b past a catch formation 173c, as shown in FIG. 12(b) (only the distal end of the recess 173b can be seen in FIG. 12(b)).

With the key 175 biased into the recess 173b by the torsional bias of the lockout spring 182 and also constrained for movement out of the recess by the catch formation 173c, the shroud 172 is now locked in position with respect to the needle guide 184 to protect the needle 118. A similar shroud arrangement is described in the Applicant's International Patent Application No. WO 2016/024085 A1, the contents of which are incorporated herein by reference.

FIG. 13(a) shows the device 300 after removal from the injection site, with the shroud 172 and the cartridge 10 empty. The firing unit 200 can be separated from the cassette 102 by pulling the two components 200, 102 apart to release the connector clips 198 of the cassette 102 from the apertures 206 of the firing unit 200. The separated firing unit 200 and cassette 102 are shown in FIG. 13(b).

The cassette 102 can be disposed of after a single use. The firing unit 200 is however reusable. To this end, the firing unit 200 can be reset by moving the drive element 208 proximally with respect to the firing unit body 202. Referring back to FIG. 7(b), as the latching member 218 passes back through the aperture 220 in the bridge part 216 of the firing unit body 202, the ramped proximal face 234 of the latching member 218 pushes the stay formation 224 aside. The stay formation 224 then moves back under the force of the latch spring 232 to engage with the latching member 218 and re-latch the delivery drive element 208. The firing unit 200 is then ready for re-use with another cassette 102.

A suitable tool, such as a rod, may be used to re-latch the delivery drive element 208. Conveniently, the rod may form part of a storage device for the firing unit 200, which could conceivably be attached to or form part of the cassette holder 194.

For instance, in the example shown in FIG. 1, the cassette holder 194 is provided with an upstanding storage rod 199 for resetting the firing unit 200. After removal of the firing unit 200 from a used cassette, the firing unit 200 can be placed on the storage rod 199. The storage rod 199 pushes the delivery drive element 208 proximally to re-latch the delivery drive element 208. The firing unit 200 can be stored on the storage rod 199 until next required.

Several variations and modifications of the above-described example are possible.

For example, although not illustrated, the hub part of the chassis may include one or more engagement formations that are arranged to engage with corresponding clip formations on the coupling element of the cartridge, so as to hold the coupling element and the hub part relative to one another in the first and/or the second attachment positions.

Alternative arrangements for forming a seal between the hub part and the piercing member can be envisioned. For example, a sealing element or O-ring may be provided to form a seal between an outer surface of the coupling element and an inner surface of the chassis.

The cartridge may differ from the example described above, and the hub part may cooperate with the cartridge to open the outlet and establish fluid communication with the needle any suitable way. For example, in place of a pierceable septum, alternative means for sealing the outlet of the chamber may be provided, such as a releasable valve. The hub part may therefore include a sealing element release member for cooperation with the sealing element to open the outlet. When a pierceable septum is provided, a double-ended needle could be used with a proximal end that acts as the piercing member.

The slit valve that closes the distal end of the second chamber of the cartridge may be replaced with any suitable valve means or closure means. For instance, a valve in the form of a duckbill valve, flap valve, umbrella valve, cross-slit valve or any other suitable valve formation could be provided, including known one-way or check valve arrangements. In general terms, the valve means may comprise any suitable closure for preventing mixing of the first and second substances. Thus, in a further example, a membrane is used to close the distal end of the second chamber. In this case, the membrane may detach, split or rupture when a sufficient pressure difference is applied across the membrane to open the distal end of the second chamber. It will be appreciated that, in some embodiments, the valve means may not re-close at the end of the mixing stroke.

The ring pull component and the retaining member could be replaced with any suitable component or arrangement for initiating the mixing stroke. For example, instead of a ring pull, a tab, slider, ribbon, cord or similar device could be used. The retaining member could be attached to a packaging part so that removal of the cassette from the packaging initiates the mixing stroke. The retaining member need not be removable from the cassette, but instead could be movable with respect to the cassette to initiate the mixing stroke. In this case, the retaining member could be directly movable by a user, or a button, slider, switch or any other suitable component or arrangement could be provided to trigger movement of the retaining member.

It will be appreciated that the operational sequence could differ from the specific example described above. For instance, in the illustrated example, the firing unit cannot be attached to the cassette before the mixing stroke has been initiated, which ensures that the mixing stroke of the cassette is correctly performed before injection. However, for some applications, the mixing stroke could instead be initiated by attachment of the firing unit, or after attachment of the firing unit. Relative movement between the hub part and the container to establish fluid communication between the container and the injection needle could occur before or after insertion of the injection needle to the injection site.

The drive mechanism of the firing unit could differ from that described above, and suitable alternative mechanisms for driving distal movement of a drive element will be known to those skilled in the art.

Similarly, any suitable trigger arrangement could be provided for initiating the drive stroke. For example, a slider, switch, pull tab or other operating member could be provided in place of the trigger button of the illustrated embodiments. It is also conceivable that the trigger arrangement could be arranged to initiate the drive stroke automatically upon contact of the device with the injection site.

The mixing mechanism used in the cassette may also differ from that described above. For example, in one alternative arrangement, a connection element is attached to the inner container to serve both as the mixing element for driving the mixing stroke and to transfer the force of the drive element to the inner container. In this case, the connection element is biased to move in the proximal direction relative to the outer container, so that the connection element draws the inner container proximally when the mixing stroke is initiated. The resulting decrease in pressure in the first chamber causes the second substance to flow through the valve to mix with the first chamber. In general terms, any mechanism for driving relative movement between the first and second containers could be employed. For example, it is conceivable that the mixing element could itself comprise a spring for driving relative movement between the first and second containers during the mixing stroke.

The present invention has been devised primarily for use with reconstitutable medicaments, in which the first medicament substance is a solid (such as a lyophilised medicament) and the second medicament substance is a liquid (such as a diluent for rehydrating the solid), the invention is not limited to use with such medicaments. The cartridge could for example be used to store and mix two liquid medicament substances. Either or both of the medicament substances could conceivably be in other forms including gels, suspensions, colloids, sols, and so on. It will be understood that, in the context of this specification, the term "mixture" is used to refer to any chemical or physical combination of two or more starting substances, and references to "mixing", "mixed" and related terms should be construed accordingly. Thus "mixing" should be taken to include the formation of a solution, suspension, emulsion, colloid, gel, sol, foam, and so on. The term "mixing" also includes the bringing together of two or more reactants that react together upon mixing to form a new chemical compound.

Further modifications and variations of the above-described examples are also possible without departing from the scope of the present invention as defined by the appended claims.

The invention claimed is:

1. A medicament delivery device system for delivery of a medicament from a cartridge comprising a first container having a first chamber for storage of a first substance, a second container at least partially received in the first container and having a second chamber for storage of a second substance, and a valve for closing a distal end of the second chamber, the system comprising:
   a disposable cassette and a reusable firing unit that is removably attachable to the cassette;
   wherein the cassette comprises:
      a body for receiving the cartridge; and
      a mixing element for displacing the second substance into the first chamber through the valve in a mixing stroke to mix with the first substance to form the medicament; and
   wherein the firing unit comprises:
      a drive element for expelling the medicament from the first chamber in a delivery stroke;
      a trigger arrangement for initiating the delivery stroke; and
      a mixing spring for biasing the mixing element for movement with respect to the cassette body.

2. The system according to claim 1, wherein the cassette is attachable to the firing unit only after the mixing stroke has been initiated.

3. The system according to claim 1, wherein the cassette comprises a release arrangement for holding the mixing element in a starting position and for releasing the mixing element to initiate the mixing stroke.

4. The system according to claim 3, wherein the release arrangement comprises a retaining member that is engageable with the mixing element to hold the mixing element in the starting position and releasable from the mixing element to initiate the mixing stroke.

5. The system according to claim 4, wherein the retaining member is removable from the cassette to initiate the mixing stroke.

6. The system according to claim 1, wherein the mixing element is moveable in a distal direction with respect to the cassette body during the mixing stroke.

7. The system according to claim 6, wherein the mixing element comprises a plunger for cooperation with a stopper of the second container.

8. The system according to claim 1, wherein the cassette comprises a connecting element for attachment to the second container, and wherein the connecting element is cooperable with the drive element of the firing unit.

9. The system according to claim 8, wherein the cassette comprises a clamping arrangement for clamping the connecting element to the second container.

10. The system according to claim 1, wherein the cassette comprises a needle holder for holding a needle for delivery of the medicament.

11. The system according to claim 10, wherein the needle holder is moveable with respect to the cassette body to extend the needle from a distal end of the cassette for insertion in an injection site.

12. The system according to claim 11, wherein movement of the needle holder is driven by the drive element of the firing unit.

13. The system according to claim 10, wherein the cassette comprises a shroud for shrouding the needle upon removal of the cassette from an injection site.

14. The system according to claim 13, wherein the shroud is biased to extend distally from a distal end of the cassette upon removal from the injection site.

15. The system according to claim 13, comprising a locking arrangement for locking the shroud in a distally extended position after removal of the cassette from the injection site.

16. The system according to claim 15, wherein the shroud is biased to rotate to activate the locking arrangement.

17. The system according to claim 1, wherein the cassette comprises a needle and a shield for enclosing the needle in an initial state of the cassette.

18. The system according to claim 17, further comprising a cassette holder, wherein the shield is attached to the cassette holder such that the shield is withdrawn from the cassette upon removal of the cassette from the cassette holder.

19. The system according to claim 18, wherein the cassette holder is arranged to hold a plurality of cassettes.

20. The system according to claim 1, wherein the cartridge comprises a sealing element for closing an outlet of the first chamber, and wherein the cassette comprises a sealing element release member for cooperation with the sealing element to open the outlet to allow delivery of the medicament.

21. The system according to claim 20, wherein the cartridge is moveable with respect to the sealing element release member from a first position in which the outlet is closed to a second position in which the sealing element release member cooperates with the sealing element to open the outlet.

22. The system according to claim 20, wherein the sealing element release member cooperates with the sealing element to open the outlet after completion of the mixing stroke.

23. The system according to claim 20, wherein the cassette comprises a seal arrangement for enclosing the sealing element release member when the outlet is closed.

24. The system according to claim 1, wherein the cassette comprises one or more connection formations for engagement with cooperable formations of the firing unit.

25. The system according to claim 1, wherein the firing unit comprises a drive spring for biasing the drive element in a distal direction.

26. The system according to claim 1, wherein the firing unit comprises a latch mechanism for holding the drive element in a starting position and for releasing the drive element upon operation of the trigger arrangement.

27. The system according to claim 26, wherein the latch mechanism comprises a stay formation that is biased for engagement with a latching member of the drive element, and wherein operation of the trigger arrangement displaces the stay formation against the bias to release the latching member.

28. The system according to claim 27, wherein the latching member is arranged to displace the stay formation against the bias to allow re-engagement of the latching member with the stay formation.

29. The cassette for use in the system of claim 1.

30. The firing unit for use in the system of claim 1.

31. A medicament delivery device comprising the cassette for use in the system of claim 1, and the firing unit for use with the cassette.

32. A cassette set comprising a plurality of the cassettes according to claim 29 and a cassette holder for holding the cassettes.

33. The cassette set according to claim 32, wherein each of the cassettes comprises a needle and a removable shield for enclosing the needle, and wherein each of the shields is attached to the cassette holder.

34. A medicament disposed in the medicament delivery device system according to claim 1.

35. A method of treating a patient having a condition susceptible to treatment with a medicament, the method comprising: dispensing an effective amount of the medicament to the patient utilizing the delivery device system according to claim 1.

36. A method of assembling a medicament delivery device for delivery of a mixture of a first substance and a second substance, wherein the first and second substances are stored in a cassette, the method comprising:
   activating a mixing mechanism of the cassette to cause mixing of the first and second substances; and
   after activating the mixing mechanism, attaching a firing unit to the cassette.

37. The method according to claim 36, further comprising removing the cassette from a cassette holder to deshield a needle of the cassette.

38. The method according to claim 36, further comprising removing an activating element from the cassette to activate the mixing mechanism.

* * * * *